(12) United States Patent
Matsushita et al.

(10) Patent No.: US 8,614,320 B2
(45) Date of Patent: *Dec. 24, 2013

(54) PREPARATION OF AMINOPYRIMIDINE COMPOUNDS

(75) Inventors: Akio Matsushita, Ube (JP); Mizuho Oda, Yamaguchi (JP); Yasuhiro Kawachi, Yamaguchi (JP); Jun-ichi Chika, Yamaguchi (JP)

(73) Assignee: AstraZeneca UK Limited, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 13/523,534

(22) Filed: Jun. 14, 2012

(65) Prior Publication Data
US 2012/0277432 A1 Nov. 1, 2012

Related U.S. Application Data

(62) Division of application No. 12/889,186, filed on Sep. 23, 2010, now Pat. No. 8,222,412, which is a division of application No. 11/933,626, filed on Nov. 1, 2007, now Pat. No. 7,816,528, which is a division of application No. 10/483,430, filed as application No. PCT/JP02/07129 on Jul. 12, 2002, now Pat. No. 7,304,156.

(30) Foreign Application Priority Data

| Jul. 13, 2001 | (JP) | 2001-213417 |
| Jul. 13, 2001 | (JP) | 2001-213418 |
| Oct. 9, 2001 | (JP) | 2001-310900 |
| Nov. 27, 2001 | (JP) | 2001-360339 |
| Jan. 16, 2002 | (JP) | 2002-007015 |
| Feb. 19, 2002 | (JP) | 2002-042076 |

(51) Int. Cl.
| C07D 239/36 | (2006.01) |
| C07D 239/42 | (2006.01) |
| C07D 239/22 | (2006.01) |
| A61K 31/505 | (2006.01) |
| A61P 3/06 | (2006.01) |

(52) U.S. Cl.
USPC .......................... 544/315; 544/316; 544/330

(58) Field of Classification Search
USPC ......................... 544/315, 316, 330
See application file for complete search history.

(56) References Cited

U.S. PATENT DOCUMENTS

| 4,613,610 A | 9/1986 | Wareing |
| 4,625,039 A | 11/1986 | Jewell, Jr. et al. |
| 4,645,858 A | 2/1987 | Lowrie et al. |
| 4,650,890 A | 3/1987 | Jewell, Jr. et al. |
| 4,677,211 A | 6/1987 | Jewell, Jr. et al. |
| 4,957,971 A | 9/1990 | Picard et al. |
| 4,968,681 A | 11/1990 | Hubsch et al. |
| 4,970,313 A | 11/1990 | Wess et al. |
| 4,977,279 A | 12/1990 | Wess et al. |
| 5,079,347 A | 1/1992 | Buch |
| 5,102,893 A | 4/1992 | Picard et al. |
| 5,260,440 A | 11/1993 | Hirai et al. |
| 5,278,313 A | 1/1994 | Thottathil et al. |
| 5,399,722 A | 3/1995 | Beck et al. |
| 5,594,153 A | 1/1997 | Thottathil et al. |
| 5,681,957 A | 10/1997 | Wolters et al. |
| 6,278,001 B1 | 8/2001 | Solladie et al. |
| 6,331,641 B1 | 12/2001 | Taoka et al. |
| 6,579,984 B1 | 6/2003 | Veith et al. |
| 6,689,591 B2 | 2/2004 | Muller et al. |
| 6,784,171 B2 | 8/2004 | Taylor et al. |

(Continued)

FOREIGN PATENT DOCUMENTS

| EP | 0252476 | 1/1988 |
| EP | 0319845 | 6/1989 |

(Continued)

OTHER PUBLICATIONS

Anne et al. "Enantioselective synthesss of key A-ring precursors of 1α, 25-dihydroxyvitamin D₃ and analogues" Synlett 9:1435-1437 (1999).

Bhaskar Reddy et al. "Enantioselective synthesis of β-hydroxy δ-lactones: a new approach to the synthetic congeners of 3-hydroxy-3-methylglutaryl coenzyme A reductase inhibitors" J. Org. Chem. 56(20):5752-5754 (1991).

Blandin et al. "One-pot and sequential asymmetric hydrogenation of β,δ-diketoesters into functionalized 1,3-diols: From anti- to syn-stereoselectivity" European Journal of Organic Chemistry 12:3421-3427 (1999).

(Continued)

*Primary Examiner* — Venkataraman Balasubramanian
(74) *Attorney, Agent, or Firm* — Morgan, Lewis & Bockius LLP

(57) ABSTRACT

A 2-(N-methyl-N-methanesulfonylamino)pyrimidine compound of the formula (3): [R is a hydrocarbyl group], is prepared by the steps of: (I) reacting an isobutyrylacetate ester with 4-fluorobenzaldehyde and urea in the presence of a protonic compound and a metal salt; (II) oxidizing the reaction product of the step (I); (III) reacting the oxidation product of the step (II) with an organic sulfonyl halide or an organic sulfonyl anhydride; and (IV) reacting the reaction product of the step (III) with N-methyl-N-methanesulfonamide.

(3)

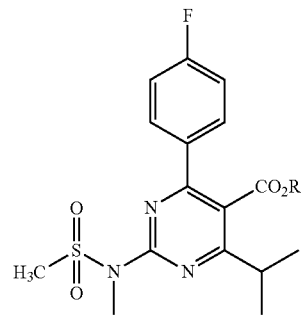

4 Claims, No Drawings

(56) References Cited

U.S. PATENT DOCUMENTS

| | | | |
|---|---|---|---|
| 6,844,437 | B1 | 1/2005 | Taylor et al. |
| 6,855,716 | B2 | 2/2005 | Ohno et al. |
| 6,870,059 | B2 | 3/2005 | Kooistra et al. |
| 7,157,255 | B2 | 1/2007 | Blacker et al. |
| 7,199,140 | B2 | 4/2007 | Hayter et al. |
| 7,304,156 | B2 | 12/2007 | Matsushita et al. |
| 7,416,865 | B2 | 8/2008 | Blacker et al. |
| 7,442,811 | B2 | 10/2008 | Bakel Van et al. |
| 7,511,140 | B2 | 3/2009 | Horbury et al. |
| 7,524,955 | B2 | 4/2009 | Newton et al. |
| 7,642,363 | B2 | 1/2010 | Kooistra et al. |
| 7,718,812 | B2 | 5/2010 | Hof et al. |
| 7,732,171 | B2 | 6/2010 | Blacker et al. |
| 7,816,528 | B2 | 10/2010 | Matsushita et al. |
| 7,842,807 | B2 | 11/2010 | Horbury et al. |
| 7,888,083 | B2 | 2/2011 | Blacker et al. |
| 7,989,643 | B2 | 8/2011 | Kooistra et al. |
| 8,034,932 | B2 | 10/2011 | Butters et al. |
| 8,063,213 | B2 | 11/2011 | Crabb et al. |
| 2003/0018199 | A1 | 1/2003 | Brodfuehrer et al. |
| 2005/0124639 | A1 | 6/2005 | Joshi et al. |
| 2006/0293355 | A1 | 12/2006 | Booth et al. |
| 2007/0093660 | A1 | 4/2007 | Tararov et al. |
| 2007/0105882 | A1 | 5/2007 | Black et al. |
| 2007/0255060 | A1 | 11/2007 | Okada et al. |
| 2008/0188657 | A1 | 8/2008 | Lenger |
| 2008/0207903 | A1 | 8/2008 | Butters et al. |
| 2008/0221323 | A1 | 9/2008 | Crabb et al. |
| 2009/0264654 | A1 | 10/2009 | Newton et al. |
| 2010/0222373 | A1 | 9/2010 | Booth et al. |
| 2010/0228028 | A1 | 9/2010 | Butters et al. |
| 2012/0059022 | A1 | 3/2012 | Booth et al. |

FOREIGN PATENT DOCUMENTS

| | | |
|---|---|---|
| EP | 0319847 | 6/1989 |
| EP | 0742212 | 11/1996 |
| EP | 0521471 | 10/2000 |
| EP | 1193259 | 4/2002 |
| GB | 2244705 | 12/1991 |
| JP | 5-178841 | 7/1993 |
| JP | 6-256318 | 9/1994 |
| WO | WO 90/03973 | 4/1990 |
| WO | WO 92/01675 | 2/1992 |
| WO | WO 93/08823 | 5/1993 |
| WO | WO 96/14846 | 4/1996 |
| WO | WO 97/19917 | 6/1997 |
| WO | WO 97/21687 | 6/1997 |
| WO | WO 99/07695 | 4/1999 |
| WO | WO 00/49014 | 8/2000 |
| WO | WO 00/78730 | 12/2000 |
| WO | WO 01/4100 | 1/2001 |
| WO | WO 01/04336 | 1/2001 |
| WO | WO 01/60804 | 8/2001 |
| WO | WO 01/72706 | 10/2001 |
| WO | WO 01/85702 | 11/2001 |
| WO | WO 01/85975 | 11/2001 |
| WO | WO 02/05519 | 1/2002 |
| WO | WO 02/06266 | 1/2002 |
| WO | WO 03/004450 | 1/2003 |
| WO | WO 03/006439 | 1/2003 |
| WO | WO 03/018555 | 3/2003 |
| WO | WO 03/059901 | 7/2003 |
| WO | WO 03/064382 | 8/2003 |
| WO | WO 03/087112 | 10/2003 |
| WO | WO 03/097614 | 11/2003 |
| WO | WO 03/106447 | 12/2003 |
| WO | WO 2004/014872 | 2/2004 |
| WO | WO 2004/052867 | 6/2004 |
| WO | WO 2004/054986 | 7/2004 |
| WO | WO 2004/103977 | 12/2004 |
| WO | WO 2004/108691 | 12/2004 |
| WO | WO 2005/023779 | 3/2005 |
| WO | WO 2005/028450 | 3/2005 |
| WO | WO 2005/042522 | 5/2005 |
| WO | WO 2005/047276 | 5/2005 |
| WO | WO 2005/063728 | 7/2005 |
| WO | WO 2005/092867 | 10/2005 |
| WO | WO 2006/067456 | 6/2006 |
| WO | WO 2006/089401 | 8/2006 |
| WO | WO 2007/007119 | 1/2007 |

OTHER PUBLICATIONS

BouzBouz et al. "Regioselective Cross-Metathesis Reaction Induced by Steric Hindrance" Organic Letters 6(20):3465-3467 (2004).

Bovy et al. "Synthesis of Heterocyclic β-Amino Acids. A convenient preparation of β-Amino-5-pyrimidinepropanoic acid and derivatives" Tetrahedron Letters 34(50):8015-8018 (1993).

Breaux et al. "An Improved General Synthesis of 4-Aryl-5-Pyrimidinecarboxylates" J. Heterocyclic Chem. 18: 183 (1981).

Casini et al. "Carbonic anhydrase inhibitors with strong topical antiglaucoma properties incorporating a 4-(2-amino-pyrimidin-4-yl-amino)-benzenesulfonamide scaffold" Journal of Enzyme Inhibition and Medicinal Chemistry 17(1):9-18 (2002).

Castro et al. "A new synthesis of 3,5-dihydroxy-7-(1-pyrrolyl)-6-heptenoic acids, a family of HMGCoA reductase inhibitors with antifungal activity" Tetrahedron Letters 43:1851-1854 (2002).

De Luca et al. "Cellulose Beads: a New Versatile Solid Support for Microwave-Assisted Synthesis. Preparation of Pyrazole and Isoxazole Libraries" J. Comb. Chem. 5(4):465 -471 (2003).

Denmark et al. "The Chemistry of Trichlorosilyl Enolates. Aldol Addition Reactions of Methyl Ketones" J. Am. Chem. Soc. 122 (37):8837-8847 (2000).

Dovlatyan et al. "Studies on functionally-substituted azines. 8. Synthesis and transformations of 1-arylsulfonylamido-4-methoxy-6-methylpyrimidines" Chemistry of Heterocyclic Compounds 36(11):1306-1313(2000).

Evans et al. "Diastereoselective synthesis of protected syn 1,3-diols by base-catalyzed intramolecular conjugate addition of hemiacetal-derived alkoxide nucleophiles" J. Org. Chem. 58:2446-2453 (1993).

Feuerstein et al. "A new efficient tetraphosphine/palladium catalyst for the Heck reaction of aryl halides with styrene or vinylether derivatives" Tetrahedron Letters 43:2191-2194 (2002).

Grohe et al. "Synthese and Reaktionen von 2,4-Dichlorpyrimidin-5-carbon-saureestem" Liebigs Ann. Chem. 1025-1035 (1973).

Gu et al. "Synthesis of ent-Haterumalide NA (ent-Oocydin A) Methyl Ester" Organic Letters 5(23):4385-4388 (2003).

Hannah et al. "Structural studies on bioactive compounds. Part 29: palladium catalysed arylations and alkynylations of sterically hindered immunomodulatory 2-amino-5-halo-4,6-(disubstituted)pyrimidines" Bioorg Med Chem. 8(4):739-750 (2000).

Hauser et al. "Synthesis of 5-phenyl-4,6-dimethyl-2-pyrimidol and derivatives from the cyclization of urea with 3-phenyl-2,4-pentanedione" Journal of Organic Chemistry 18(5): 588-593 (1953).

Hiyama et al. "Synthesis of Artificial HMG-CoA Reductase Inhibitors Based on the Olefination Strategy" Bull. Chem. Soc. Jpn. 68 (1):364-372 (1995).

Kaneko et al. "Preparation of optically active 5,6-epoxyhexanoic acid esters as materials for physiologically active substances" Chemical Abstracts +Indexes, American Chemical Society, Columbus, US 118(11):832 (1993).

Littke et al. "A Versatile Catalyst for Heck Reactions of Aryl Chlorides and Aryl Bromides under Mild Conditions" J. Am. Chem. Soc. 123(29):6989-7000 (2001).

Littke et al. "Heck reactions in the presence of P(t-Bu)$_3$: Expanded scope and milder reaction conditions for the coupling of aryl chlorides" J. Org. Chem. 64:10-11 (1999).

Ma et al. "Lanthanide Triflate Catalyzed Biginelli Reaction, One-Pot Synthesis of Dihydropyrimidinones under Solvent Free Conditions" Journal of Organic Chemistry, 2000 65(12), 3864-3868.

Menges et al. "Oxidative Degradation of γ-Butyrolactons into 1,3-Diols via a Criegee Rearrangement of Peroxosulfonates. An Enantioselective Synthesis of Compactin Lactone and its Diastereomer" Synlett 12:901-905 (1993).

(56) References Cited

OTHER PUBLICATIONS

Miller et al. "Discovery of Aminopyridine-Based Inhibitors of Bacterial Enoyl-ACP Reductase (FabI)" J. Med. Chem. 45(15):3246-3256 (2002).

Minami et al. "A Novel Enantioselective Synthesis of HMG Co-A Reductase Inhibitor NK-104 and a Related Compound" Tetrahedron letters 33(49):7525-7526 (1992).

Minami et al. "Stereoselective Reduction of β,δ-Diketo Esters Derived From Tartaric Acid. A Facile Route to Optically Active 6-oxo-3,5-*syn*-isopropylidenedioxyhexanoate, a Versatile Synthetic Intermediate of Artificial HMG Co-A Reductase Inhibitors" Tetrahedron Letters 34(3):513-516 (1993).

Mohr et al. "Stereoselective synthesis of functionalized erythro/1,3-diols" Tetrahedron Letters 28(4):391-394 (1987).

Moore et al. "Biosynthesis of the hypocholesterolemic agent mevinolin by *Aspergillus terreus*. Determination of the origin of carbon, hydrogen, and oxygen atoms by carbon-13 NMR and mass spectrometry" J. Am. Chem. Soc. 107(12): 3694-3701 (1985).

Prasad et al. "A novel diastereroselective synthesis of lactone moiety of compactin" Tetrahedron Letters 25(23):2435-2438 (1984).

Presentation given at the 20th International Congress of Heterocyclic Chemistry in Palermo, Aug. 1-5, 2005.

Presentation given at the Gordon Conference on Heterocyclic Compounds, Salve Regina University, Newport, Rhode Island, Jul. 4-9, 2004.

Sakaki et al. "Lipase-catalyzed asymmetric synthesis of 6-(3-chloro-2-hydroxypropyl)-1,3-dioxin-4-ones and their conversion to chiral 5,6-epoxyhexanoates" Tetrahedron: Asymmetry 2(5):343-346 (1991).

Scialdone et al. "Building blocks for skipped polyols: syn-1,3-acetonides by chemoenzymatic synthesis from cycloheptatriene" Tetrahedron Letters 36(1):43-46 (1995).

Shao et al. "Asymmetric hydrogenation of 3,5-Dioxoesters catalyzed by Ru-binap complex: A short step asymmetric synthesis of 6-substituted 5,6-dihydro-2-pyrones" Tetrahedron 49(10):1997-2010 (1993).

Singer et al. "Catalytic, enantioselective dienolate additions to aldehydes: Preparation of optically-active acetoacetate aldol adducts" Journal of the American Chemical Society 117(49):12360-12361 (1995).

Solladié et al. "Chrial Sulfoxides in Asymmetric Synthesis: Enantioselective Synthesis of the Lactonic Moiety of (+)-Compactin and (+)-Mevinolin. Application of a Compactin Analogue" J. Org. Chem. 60:7774-7777 (1995).

Takahashi et al. "Synthesis of an artificial HMG-CoA reductase inhibitor NK-104 via a hydrosilylation-cross-coupling reaction" Bulletin of the Chemical Society of Japan 68(9):2649-2656 (1995).

Vanden Eynde et al. "Microwave-mediated Regioselective Synthesis of. Novel Pyrimido[1,2-a]pyrimidines under Solvent-free Conditions" Tetrahedron 57(9):1785-1791 (2001).

Virolleaud et al. "A straightforward synthesis of (*E*)-δ-alkenyl-β,γ-unsaturated δ-lactones by a tandem ring-closing/cross-coupling metathesis process" Tetrahedron Letters 44(44):8081-8084 (2003).

Watanabe et al Bioorganic & Medicinal Chemistry, vol. 5, No. 2, 1997, pp. 437-444.

Wess et al. "Stereoselective Synthesis of HR 780 a New Highly Potent HMG-CoA Reductase Inhibitor", Tetrahedron Letters 31(18): 2545-2548 (1990).

Zakrzewski et al. "Synthesis of syn- and anti-3,5-Dihydroxy-6-heptenoates from 2-Deoxy-d-ribose: Intermediates for Polyols Synthesis" Synlett 2:215-218 (2003).

PREPARATION OF AMINOPYRIMIDINE COMPOUNDS

RELATED APPLICATIONS

This application is a Divisional of U.S. application Ser. No. 12/889,186 filed Sep. 23, 2010, now allowed, which is a Divisional application of U.S. application Ser. No. 11/933,626 filed Nov. 1, 2007, now U.S. Pat. No. 7,816,528, which is a Divisional application of U.S. application Ser. No. 10/483,430, filed Jan. 12, 2004, now U.S. Pat. No. 7,304,156, which is a U.S. National Phase Application of International Application No. PCT/JP02/07129, filed Jul. 12, 2002, which claims the benefit of Japanese Patent Application No. 2001-213417, filed Jul. 13, 2001, Japanese Patent Application No. 2001-213418, filed Jul. 13, 2001, Japanese Patent Application No. 2001-310900, filed Oct. 9, 2001, Japanese Patent Application No. 2001-360339, filed Nov. 27, 2001, Japanese Patent Application No. 2002-07015, filed Jan. 16, 2002, and Japanese Patent Application No. 2002-042076, filed Feb. 19, 2002, all of which are herein incorporated by reference in their entireties.

FIELD OF THE INVENTION

The present invention relates to the preparation of aminopyrimidine compounds having the following formula (8):

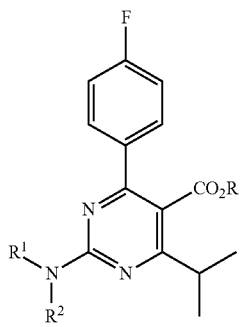

(8)

[in the formula (8), R is a hydrocarbyl group, and each of $R^1$ and $R^2$ independently is a hydrogen atom, an alkyl group, an alkylsulfonyl group, or an arylsulfonyl group], more particularly to the preparation of a 2-(N-methyl-N-methanesulfonylamino)pyrimidine compound having the following formula (3):

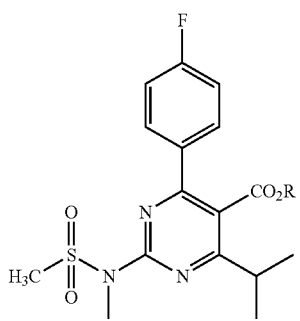

(3)

wherein R represents a hydrocarbyl group.

BACKGROUND OF THE INVENTION

Bioorg. Med. Chem., 5, 437 (1997) describes that the 2-(N-methyl-N-methanesulfonylamino)pyrimidine compound is employable as an intermediate compound for producing a cholesterol reducing agent (HMG-CoA reductase inhibitor: S-4522) having the following formula:

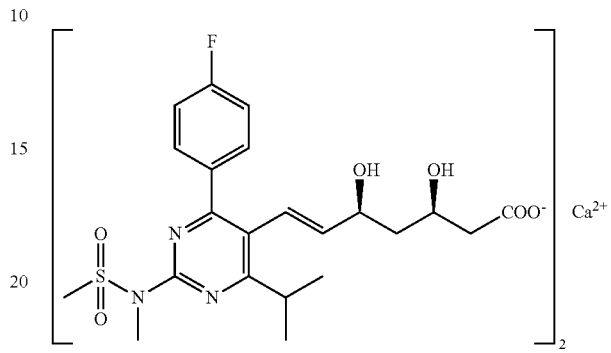

and which is now generally known as the calcium salt of rosuvastatin or rosuvastatin calcium.

WO 01/04100 describes a process for preparing the 2-(N-methyl-N-methanesulfonylamino)pyrimidine compound which comprises the steps of:

reacting methyl isobutyrylacetate with 4-fluoro-benzonitrile to produce methyl 2-[1-amino-1-(4-fluorophenyl)methylene]-4-methyl-3-oxopentanate; and reacting the 2-[1-amino-1-(4-fluorophenyl)methylene]-4-methyl-3-oxopentanate with N-cyano-N-methyl-methanesulfonamide which is obtained by reaction between N-methylmethanesulfonamide and cyanogen chloride, to produce 4-(4-fluorophenyl)-6-isopropyl-5-methoxycarbonyl-2-(N-methanesulfonyl-N-methylamino)pyrimidine.

It is described that the total yield (based on the amount of methyl isobutyrylacetate) is 45.5%.

It appears that the process described in WO 01/04100 is disadvantageous for the industrial preparation, because the yield is not high and it is necessary to employ toxic cyanogen chloride as one of the starting compounds.

Accordingly, it is an object of the invention to provide a novel process for preparing a 2-(N-methyl-N-methanesulfonylamino)pyrimidine or an analogous amino-pyrimidine compound thereof, more particularly to provide a novel process which provides the compound more conveniently and/or without employing a toxic compound and/or provides the compound in high yield and/or high purity.

It is another object of the invention to provide a novel process for preparing a 2-(N-methyl-N-methanesulfonylamino)pyrimidine compound or an analogous amino-pyrimidine compound thereof which is favorably employable in the industrial preparation.

SUMMARY OF THE INVENTION

The present invention resides in a process for preparing a 2-(N-methyl-N-methanesulfonylamino)pyrimidine having the formula (3):

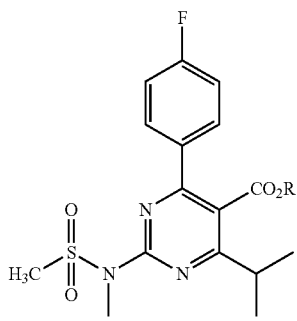
(3)

[R is a hydrocarbyl group],
which comprises the steps of:
reacting a hydroxypyrimidine compound having the formula (1):

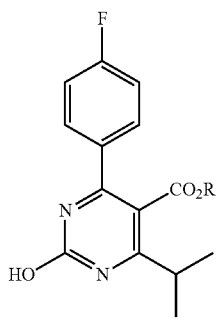
(1)

in which R is the same as above,
with an organic sulfonyl halide having the formula (2):

R'SO$_2$X    (2)

in which R' is a hydrocarbyl group and X is a halogen atom, or an organic sulfonic anhydride having the formula (2a):

(R'SO$_2$)$_2$O    (2a)

in which R' is the same as above, and reacting the resulting reaction product with N-methyl-N-methanesulfonamide.

The invention also resides in a hydroxypyrimidine compound having the above-identified formula (1).

The invention further resides in a method for preparing a hydroxypyrimidine compound of the formula (1), which comprises oxidizing a dihydropyrimidinone compound having the formula (4):

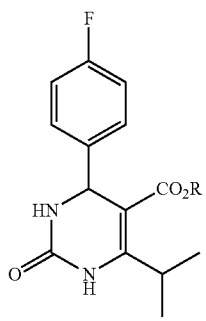
(4)

wherein R is a hydrocarbyl group.

The invention further resides in a dihydropyrimidinone compound having the formula (4).

The invention furthermore resides in a method for preparing a dihydropyrimidinone compound of the formula (4), which comprises reacting an isobutyrylacetate ester having the formula (5):

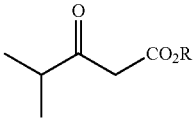
(5)

in which R is a hydrocarbyl group,
with 4-fluorobenzaldehyde and urea in the presence of a protonic compound and a metal salt.

The invention furthermore resides in a method for preparing an aminopyrimidine compound having the formula (8):

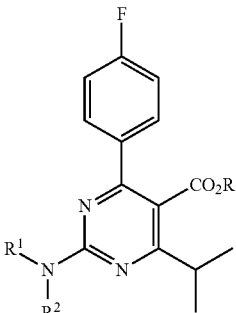
(8)

wherein R is a hydrocarbyl group, and each of $R^1$ and $R^2$ independently is hydrogen atom, an alkyl group, an alkylsulfonyl group, or an arylsulfonyl group, which comprises reacting a 2-substituted pyrimidine compound having the formula (6):

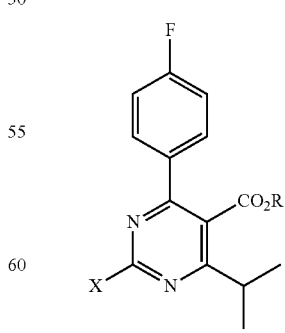
(6)

wherein R is the same as above, and X is a halogen atom or an organic sulfonyloxy group, with an amine compound having the formula (7):

 (7)

wherein each of $R^1$ and $R^2$ is the same as above.

The invention furthermore resides in a halogenopyrimidine compound having the formula (9):

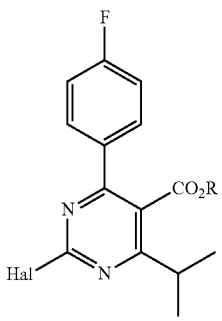 (9)

wherein R is a hydrocarbyl group, and Hal is a halogen atom.

The invention furthermore resides in a method for preparing the halogenopyrimidine compound of the formula (9), which comprises reacting a hydroxypyrimidine compound of the aforementioned formula (1) with a halogenating agent.

The invention furthermore resides in an organic sulfonyloxypyrimidine compound having the formula (10):

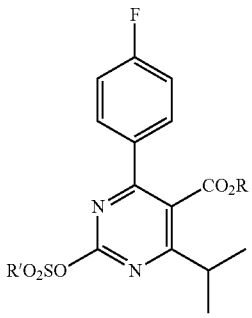 (10)

wherein each of R and R' independently is a hydrocarbyl group.

The invention furthermore resides in a method for preparing an organic sulfonyloxypyrimidine compound of the formula (10), which comprises reacting a hydroxypyrimidine compound of the aforementioned formula (1) with an organic sulfonyl halide having the formula (2):

R'SO$_2$X (2)

wherein R' is a hydrocarbyl group, and X is a halogen atom, or an organic sulfonic anhydride having the formula (2a):

(R'SO$_2$)$_2$O (2a)

in which R' is the same as above.

The invention furthermore resides in a process for preparing a 2-(N-methyl-N-methanesulfonylamino)pyrimidine of the formula (3) which comprises the steps of:

(I) reacting an isobutyrylacetate ester of the formula (5) with 4-fluorobenzaldehyde and urea in the presence of a protonic compound and a metal salt;

(II) oxidizing the reaction product of the step (I);

(III) reacting the oxidation product of the step (II) with an organic sulfonyl halide of the formula (2) or an organic sulfonic anhydride of the formula (2a); and (IV) reacting the reaction product of the step (III) with N-methyl-N-methanesulfonamide.

In the above-mentioned process, the steps (III) and (IV) can be carried out continuously in the same reaction mixture.

DETAILED DESCRIPTION OF THE INVENTION

The representative process for the preparation of 2-(N-methyl-N-methanesulfonylamino)pyrimidine of the formula (3) according to the present invention is schematically illustrated as follows:

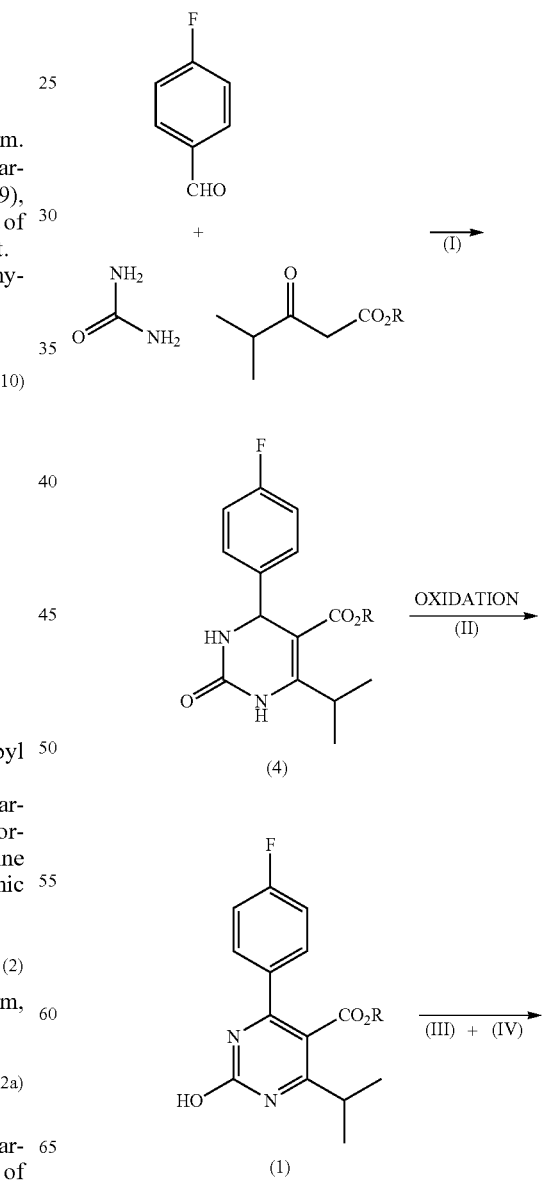

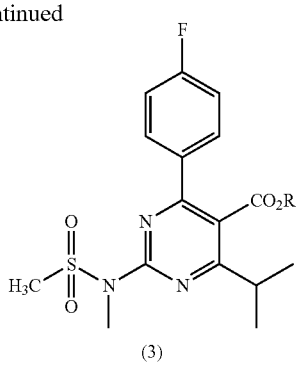

(3)

Each step in the above-illustrated reaction scheme is described below in more detail.

Step (I)

In the step (I), an isobutyrylacetate ester of the following formula (5):

(5)

[R is a hydrocarbyl group]
is reacted with 4-fluorobenzaldehyde and urea in the presence of a protonic compound and a metal salt.

The hydrocarbyl group (i.e., hydrocarbon group) represented by R in the formulas of the compounds involved in the reactions of the invention can be an alkyl group such as methyl, ethyl, propyl, butyl, pentyl, hexyl, heptyl, octyl, nonyl, or decyl, more particularly an alkyl group having 1-6 carbon atoms and especially an alkyl group having 1-4 carbon atoms; a cycloalkyl group such as cyclopropyl, cyclobutyl, cyclopentyl, or cyclohexyl; an aralkyl group such as benzyl, phenylethyl, or phenylpropyl; or an aryl group such as phenyl or methylphenyl. The hydrocarbyl group can take any isomer configurations such as normal, iso, and tertiary. The hydrocarbyl group can have one or more substituents, provided that the substituents do not disturb the reaction involved.

The protonic compound can be an inorganic acid or its salt such as hydrochloric acid, sulfuric acid, potassium hydrogensulfate, sodium hydrogen sulfate, nitric acid, or phosphoric acid; an organic sulfonic acid such as methanesulfonic acid, ethanesulfonic acid, benzenesulfonic acid, p-toluenesulfonic acid, or p-bromobenzenesulfonic acid; an organic carboxylic acid such as acetic acid, propionic acid, butyric acid, or benzoic acid; an alcohol such as methanol, ethanol, or propanol. Preferred are protonic acids such as hydrochloric acid, sulfuric acid, p-toluenesulfonic acid, and acetic acid. Most preferred is sulfuric acid. The protonic compounds can be employed singly or in combination.

The protonic compound can be employed in an amount of, preferably, 0.01 to 3 mol., more preferably 0.1 to 1 mol., per one mol. of the isobutyrylacetate ester.

The metal salt employed in the reaction can be copper(I) chloride, copper(II) chloride, copper(II) acetate, iron(II) chloride, iron(III) chloride, aluminum chloride, nickel(II) bromide, tin(IV) chloride, titanium tetrachloride, or magnesium bromide. Preferred are copper(I) chloride, copper(II) chloride, iron(III) chloride and nickel(II) bromide. Most preferred is copper(I) chloride. The metal salts may contain water of crystallization. The metal salts can be employed singly or in combination.

The metal salt can be employed in an amount of, preferably, 0.001 to 5 mol., more preferably 0.01 to 0.1 mol., per one mol. of the isobutyrylacetate ester.

The 4-fluorobenzaldehyde can be employed in an amount of, preferably, 0.5 to 10 mol., more preferably 0.9 to 1.1 mol., per one mol. of the isobutyrylacetate ester.

The urea can be employed in an amount of, preferably, 0.5 to 10 mol., more preferably 1.5 to 2 mol., per one mol. of the isobutyrylacetate ester.

The reaction can be performed in the presence or absence of a solvent. There are no specific limitations with respect to the solvent employed, so far as the solvent does not disturb the desired reaction. Examples of the employable solvents include alcohols such as methanol, ethanol, n-propyl alcohol, isopropyl alcohol, n-butyl alcohol, isobutyl alcohol, sec-butyl alcohol, and t-butyl alcohol; ethers such as diethyl ether, diisopropyl ether, tetrahydrofuran, and dimethoxyethane; nitriles such as acetonitrile, propionitrile, butyronitrile, and isobutyronitrile; halogenated aliphatic hydrocarbons such as dichloromethane, dichloroethane, chloroform, and carbon tetrachloride; aromatic hydrocarbons such as benzene, toluene, and xylene; halogenated aromatic hydrocarbons such as chlorobenzene; and nitrated aromatic hydrocarbons such as nitrobenzene. Preferred are methanol, ethanol, n-propyl alcohol, isopropyl alcohol, n-butyl alcohol, diisopropyl ether, tetrahydrofuran, dimethoxyethane, acetonitrile, butyronitrile, isobutylonitrile, dichloromethane, dichloroethane, chloroform, toluene, xylene, and chlorobenzene. Especially preferred are methanol, ethanol, and isopropyl alcohol. The solvents can be employed singly or in combination.

The solvent can be employed in an amount of, preferably 0.1 to 10 liters, more preferably 0.3 to 2 liters, per one mole of the isobutyrylacetate ester. The amount may vary depending on homogeneity and dispersability of the reaction mixture.

The reaction can be conducted by reacting the isobutyrylacetate ester, 4-fluorobenzaldehyde, and urea, in a solvent in the presence of a protonic compound and a metal salt under inert gas atmosphere. The reaction can be carried out at a temperature of, preferably −10 to 200° C., more preferably 30 to 100° C. There are no specific limitations with respect to the surrounding pressure.

The resulting product of the reaction, that is, a dihydropyrimidinone compound of the formula (4), can be isolated and purified according to the conventional procedures such as distillation, crystallization, recrystallization, and column chromatography.

Step (II)

In the step (II), a dihydropyrimidinone compound of the formula (4), that is, the reaction product of the step (I), is oxidized to give a hydroxypyrimidine compound of the formula (1).

The oxidation (or dehydrogenation oxidation) can be performed in various conventional manners. Preferred is oxidation utilizing nitric acid, because this oxidation procedure is easily carried out and the post-treatment of the reaction product is easy.

The nitric acid can be employed in an amount of, preferably 1 to 20 mol., more preferably 3 to 15 mol., per one mole of the dihydropyrimidinone compound of the formula (4). The nitric acid of a concentration of, preferably 40 to 80%, more preferably 50 to 70%, can be preferably employed.

The oxidation can be performed in the presence or absence of a solvent. There are no specific limitations with respect to the solvent employed, so far as the solvent does not disturb the desired reaction. Examples of the preferred solvents include carboxylic acids such as acetic acid, propionic acid, and butyric acid. The solvents can be employed singly or in combination.

The solvent can be employed in an amount of, preferably 0.1 to 7 mL, more preferably 0.5 to 3 mL, per 1 g of the dihydropyrimidinone compound. The amount may vary depending on homogeneity and dispersability of the reaction mixture.

The oxidation can be conducted by reacting the dihydropyrimidinone compound and nitric acid in a solvent under inert gas atmosphere. The oxidation can be carried out at a temperature of, preferably −10 to 100° C., more preferably 0 to 50° C. There are no specific limitations with respect to the surrounding pressure. A reaction initiator such as sodium nitrite may be incorporated into the reaction system to accelerate the oxidation rate.

The resulting product of the reaction, that is, the hydroxypyrimidine compound of the formula (1), can be isolated and purified according to the conventional procedures such as distillation, crystallization, recrystallization, and column chromatography.

Steps (III) and (IV)

In the steps (III) and (IV), a hydroxypyrimidine compound of the formula (1), that is, the reaction product of the step (II), is reacted with an organic sulfonyl halide of the formula (2):

R'SO$_2$X    (2)

or an organic sulfonic anhydride of the formula (2a):

(R'SO$_2$)$_2$O    (2a)

and reacting the resulting reaction product with N-methyl-N-methanesulfonamide.

In the formulas (2) and (2a), R' is a hydrocarbyl group which can have one or more substituents. Examples of the hydrocarbyl groups include alkyl groups such as methyl, ethyl, propyl, butyl, pentyl, heptyl, octyl, nonyl, and decyl, more particularly an alkyl group having 1-6 carbon atoms and especially an alkyl group having 1-4 carbon atoms; fluorinated alkyl groups such as trifluoromethyl, nonafluorobutyl, tridecafluorohexyl, heptadecafluorooctyl, and uncosafluorodecyl; cycloalkyl groups such as cyclopropyl, cyclobutyl, cyclopentyl, and cyclohexyl; aralkyl groups such as benzyl, phenylethyl, and phenylpropyl; and aryl groups, including unsubstituted and substituted phenyl or naphthyl groups, such as phenyl, naphthyl, tolyl, xylyl, mesityl, triisopropylphenyl, methoxyphenyl, chlorophenyl, and nitrophenyl. Thus, the hydrocarbyl group can have one or more substituents, provided that the substituents do not disturb the reaction involved. The hydrocarbyl group can take any isomer configurations such as normal, iso, and tertiary. A particularly suitable value for R' when it is aryl includes, for example, a phenyl or naphthyl group (particularly phenyl) which is unsubstituted or bears 1, 2 or 3 substituents. The substituents may be independently selected from, for example, alkyl having 1-4 carbon atoms, alkoxy having 1-4 carbon atoms, halogeno, and nitro.

In the formula (2), X is a halogen atom such as fluorine, chlorine, bromine, and iodine.

Examples of the sulfonyl halides include methanesulfonyl fluoride, methanesulfonyl chloride, ethanesulfonyl chloride, 1-propanesulfonyl chloride, 2-propanesulfonyl chloride, trifluoromethanesulfonyl fluoride, trifluoromethanesulfonyl chloride, nonafluorobutanesulfonyl fluoride, tridecafluorohexanesulfonyl fluoride, heptadecafluorooctanesulfonyl fluoride, uncosafluorodecanesulfonyl fluoride, benzenesulfonyl chloride, 1-naphthalenesulfonyl chloride, 2-naphthalenesulfonyl chloride, p-toluenesulfonyl fluoride, p-toluenesulfonyl chloride, 2,4,6-trimethylbenzenesulfonyl chloride, 2,4,6-triisopropylbenzenesulfonyl chloride, p-methoxybenzenesulfonyl chloride, p-chlorobenzenesulfonyl chloride, and 2-nitrobenzenesulfonyl chloride. Preferred are trifluoromethanesulfonyl fluoride, benzenesulfonyl chloride, 1-naphthalenesulfonyl chloride, 2-naphthalenesulfonyl chloride, p-toluenesulfonyl chloride, 2,4,6-trimethylbenzenesulfonyl chloride, 2,4,6-triisopropylbenzenesulfonyl chloride, p-methoxybenzenesulfonyl chloride, and p-chlorobenzenesulfonyl chloride. Particularly preferred are p-toluenesulfonyl chloride, 2,4,6-trimethylbenzenesulfonyl chloride, 2,4,6-triisopropylbenzenesulfonyl chloride, and p-methoxybenzenesulfonyl chloride.

Examples of the sulfonic anhydrides include methanesulfonic anhydride, trifluoromethanesulfonic anhydride, benzenesulfonic anhydride, and p-toluenesulfonic anhydride. Preferred are trifluoromethanesulfonic anhydride, benzenesulfonic anhydride, and p-toluenesulfonic anhydride. Particularly preferred are trifluoromethanesulfonic anhydride and p-toluenesulfonic anhydride.

The sulfonyl halide or sulfonic anhydride can be employed in an amount of, preferably 0.1 to 20 mol., more preferably 0.5 to 5 mol., most preferably 1 to 2 mol., per one mole of the hydroxypyrimidine compound.

In the subsequent step, N-methylmethanesulfonamide can be employed in an amount of, preferably 0.1 to 30 mol., more preferably 1 to 5 mol., per one mol. of the hydroxypyrimidine compound.

The reactions of the steps (III) and (IV) can be preferably performed in the presence of a base. Examples of the bases include alkali metal carbonates such as sodium carbonate and potassium carbonate; alkali metal hydrogencarbonates such as sodium hydrogencarbonate; alkali metal hydroxides such as lithium hydroxide, sodium hydroxide and potassium hydroxide; alkali metal alkoxides such as sodium methoxide, sodium t-butoxide, potassium t-butoxide, and sodium t-pentoxide; and tertiary amines such as triethylamine, triisopropylamine, diisopropylethylamine, and pyridine. Preferred are sodium carbonate, potassium carbonate, potassium t-butoxide, sodium t-pentoxide, triethylamine, and pyridine. Particularly preferred are potassium carbonate, sodium t-pentoxide, and triethylamine. Most preferred are potassium carbonate and sodium t-pentoxide. The bases can be employed singly or in combination.

The base can be employed in an amount of, preferably 0.1 to 30 mol., more preferably 1 to 5 mol., per one mol. of the hydroxypyrimidine compound. The whole amount of the base can be incorporated in the reaction system before the reaction begins, or the base can be portionwise added to the reaction system after the reaction begins.

The reaction can be performed in the presence or absence of a solvent. There are no specific limitations with respect to the solvent, so far as the solvent does not disturb the reaction. Examples of the solvents include water; ketones such as acetone, methyl ethyl ketone, and diethyl ketone; ethers such as diethyl ether and tetrahydrofuran; esters such as ethyl acetate, propyl acetate, and butyl acetate; nitriles such as acetonitrile and propionitrile; amides such as N,N-dimethylformamide and N-methylpyrrolidone; sulfoxides such as dimethylsulfoxide; ureas such as N,N'-dimethylimidazolinone. Preferred are acetone, tetrahydrofuran, ethyl acetate, butyl acetate, acetonitrile, N,N-dimethylformamide, and dimethylsulfoxide. Particularly preferred are ethyl acetate, butyl acetate and acetonitrile. Most preferred are butyl acetate and acetonitrile. The solvents can be employed singly or in combination.

The solvent can be employed in an amount of, preferably 0.01 to 100 liters, more preferably 0.5 to 5 liters, per one mole of the hydroxypyrimidine compound. The amount may vary depending on homogeneity and dispersability of the reaction mixture.

The reaction can be performed by reacting the hydroxypyrimidine compound and the organic sulfonyl halide or sulfonic anhydride in a solvent in the presence of a base with stirring under inert gas atmosphere. The base can be added portionwise. The reaction can be carried out at a temperature of, preferably −30 to 250° C., more preferably 0 to 150° C. There are no specific limitations with respect to the surrounding pressure.

The resulting product of the reaction, that is, the 2-(N-methyl-N-methanecarbonsulfonylamino)pyrimidine compound of the formula (3), can be isolated and purified according to the conventional procedures such as distillation, crystallization, recrystallization, and column chromatography.

The 2-(N-methyl-N-methanesulfonylamino)pyrimidine compound of the formula (3) and other pyrimidine compounds of the formula (8) can be prepared from a hydroxypyrimidine compound of the formula (1) via a 2-substituted pyrimidine compound of the formula (6) in the following steps (V) and (VI):

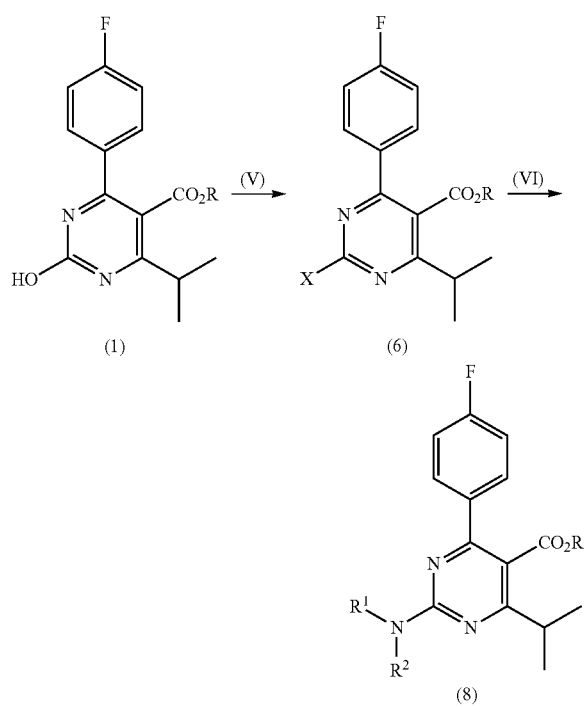

In the formula (8), R has the same meaning as described above, and each of $R^1$ and $R^2$ independently is a hydrogen atom, an alkyl group, an alkylsulfonyl group, or arylsulfonyl group.

Step (V)

In the step (V), a hydroxypyrimidine compound of the formula (1) is reacted with a halogenating agent such as a chlorinating agent, an organic sulfonyl halide of the formula (2):

$$R'SO_2X \qquad (2)$$

in which R' has the same meaning as above and X is a halogen atom, or an organic sulfonic anhydride of the formula (2a):

$$(R'SO_2)_2O \qquad (2a)$$

in which R' has the same meaning as above.

Examples of the halogenating agents include phosphorus oxychloride and thionyl chloride. The halogenating agents can be employed singly or in combination.

The halogenating agent can be employed in an amount of, preferably 0.1 to 50 mol., more preferably 1 to 20 mol., most preferably 1.5 to 10 mol., per one mol. of the hydroxypyrimidine compound.

Examples of the organic sulfonyl halides and sulfonic anhydrides are those described hereinbefore.

The organic sulfonyl halide or sulfonic anhydride can be employed in an amount of, preferably 0.1 to 20 mol., more preferably 0.5 to 5 mol., most preferably 1 to 2 mol., per one mol. of the hydroxypyrimidine compound.

The reaction can be performed in the presence or absence of a solvent. There are no specific limitations with respect to the solvent, so far as the solvent does not disturb the reaction. Examples of the solvents include aromatic hydrocarbons such as toluene; halogenated aromatic hydrocarbons such as chlorobenzene; nitrated hydrocarbons such as nitrobenzene; halogenated aliphatic hydrocarbons such as methylene chloride and 1,2-dichloroethane; amides such as N,N-dimethylformamide; water (not for a halogenating agent); nitriles such as acetonitrile and propionitrile; carboxylic acid esters such as ethyl acetate, propyl acetate, butyl acetate; ketones such as acetone, methyl ethyl ketone, diethyl ketone; and ethers such as diethyl ether and tetrahydrofuran. Preferred are butyl acetate, toluene, methylene chloride, acetonitrile, chlorobenzene, nitrobenzene, and N,N-dimethylformamide. The solvents can be employed singly or in combination.

The solvent can be employed in the reaction utilizing the halogenating agent in an amount of, preferably 0.01 to 10 liters, more preferably 0.1 to 2 liters, per one mole of the hydroxypyrimidine compound. The amount may vary depending on homogeneity and dispersability of the reaction mixture.

The solvent can be employed in the reaction utilizing the sulfonyl chloride or sulfonic anhydride in an amount of, preferably 0.1 to 50 liters, more preferably 0.5 to 2 liters, per one mole of the hydroxypyrimidine compound. The amount may vary depending on homogeneity and dispersability of the reaction mixture.

The reaction can be carried out by reacting the hydroxypyrimidine compound and the halogenating agent, in a solvent with stirring under inert gas atmosphere. The reaction can be carried out at a temperature of, preferably 0 to 200° C., more preferably 50 to 120° C. There are no specific limitations with respect to the surrounding pressure.

The reaction can be carried out by reacting the hydroxypyrimidine compound and the sulfonyl halide or sulfonyl anhydride in a solvent with stirring under inert gas atmosphere. The reaction can be carried out at a temperature of, preferably −30 to 200° C., more preferably 0 to 50° C. There are no specific limitations with respect to the surrounding pressure.

The resulting product of the reaction, that is, a 2-substituted pyrimidine compound such as a chloropyrimidine compound or a sulfonyloxypyrimidine compound, can be isolated and purified according to the conventional procedures such as distillation, crystallization, recrystallization, and column chromatography.

Step (VI)

In the step (VI), the 2-substituted pyrimidine compound, such as a chloropyrimidine compound or a sulfonyloxypyrimidine compound prepared in the step (V) is reacted with an amine compound having the formula (7):

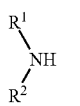
(7)

wherein each of $R^1$ and $R^2$ is the same as above.

Examples of the groups of $R^1$ and $R^2$ include a hydrogen atom, alkyl groups such as methyl, ethyl, propyl, butyl, pentyl and hexyl; alkylsulfonyl groups such as methanesulfonyl; and arylsulfonyl groups such as benzenesulfonyl and p-toluenesulfonyl.

The amine compound can be employed in an amount of, preferably 0.1 to 30 mol., more preferably 1 to 5 mol., per one mol. of the 2-substituted pyrimidine compound.

The reaction is preferably performed in the presence of a base. Examples of the bases are those described hereinbefore. The base can be preferably employed in an amount of, preferably 0.1 to 30 mol., more preferably 1 to 5 mol., per one mol. of the 2-substituted pyrimidine compound.

The reaction can be performed in the presence or absence of a solvent. There are no specific limitations with respect to the solvent, so far as the solvent does not disturb the reaction. Examples of the solvents include water; ketones such as acetone, methyl ethyl ketone, and diethyl ketone; ethers such as diethyl ether and tetrahydrofuran; esters such as ethyl acetate, propyl acetate, and butyl acetate; nitriles such as acetonitrile and propionitrile; amides such as N,N-dimethylformamide and N-methylpyrrolidone; sulfoxides such as dimethylsulfoxide; ureas such as N,N'-dimethylimidazolidinone. Preferred are acetone, tetrahydrofuran, ethyl acetate, butyl acetate, acetonitrile, N,N-dimethylformamide, and dimethylsulfoxide. Particularly preferred are ethyl acetate, butyl acetate and acetonitrile. The solvents can be employed singly or in combination.

The solvent can be employed in an amount of, preferably 0.01 to 100 liters, more preferably 0.5 to 5 liters, per one mole of the 2-substituted pyrimidine compound. The amount may vary depending on homogeneity and dispersability of the reaction mixture.

The reaction can be conducted by reacting the 2-substituted pyrimidine compound and the amine compound in a solvent in the presence of a base with stirring under inert gas atmosphere. The reaction can be carried out at a temperature of, preferably −20 to 250° C., more preferably 25 to 150° C. There are no specific limitations with respect to the surrounding pressure.

The reaction can be conducted in two separate liquid phases in the presence of a phase transfer catalyst. Examples of the phase transfer catalysts include tetramethylammonium chloride, tetramethylammonium bromide, tetraethylammonium fluoride, tetraethylammonium chloride, tetraethylammonium bromide, tetrapropylammonium bromide, tetrapropylammonium iodide, tetrabutylammonium fluoride, tetrabutylammonium chloride, tetrabutylammonium bromide, tetrabutylammonium iodide, tetrapentylammonium bromide, tetrahexylammonium bromide, tetraheptylammonium bromide, tetraoctylammonium bromide, benzyldimethyltetradecylammonium chloride, benzyltriethylammonium chloride, phenyltrimethylammonium chloride, phenyltrimethylammonium iodide, and hexadecyltrimethylammonium chloride. Preferred are tetrabutylammonium chloride, tetrabutylammonium bromide, tetrabutylammonium iodided, benzyltriethylammonium chloride, and hexadecyltrimethylammonium chloride. Most preferred are tetrabutylammonium bromide, benzyltriethylammonium chloride, and hexadecyltrimethylammonium chloride.

The phase transfer catalyst can be employed in an amount of 0.01 to 0.5 mol., preferably 0.05 to 0.2 mol., per one mol. of the 2-substituted pyrimidine compound.

The resulting product of the reaction, that is, a 2-(N-methyl-N-methanesulfonylamino)pyrimidine compound of the formula (3) or other aminopyrimidine compounds of formula (8), can be isolated and purified according to the conventional procedures such as distillation, crystallization, recrystallization, or column chromatography.

The present invention is further described by the following non-limiting examples.

Example 1

Preparation of 4-(4-fluorophenyl)-6-isopropyl-5-methoxycarbonyl-3,4-2(1H)-dihydropyrimidinone In a 500 mL-volume glass flask equipped with a stirrer, a thermometer and a reflux condenser were placed 28.8 g (0.2 mol.) of methyl isobutyrylacetate, 24.8 g (0.2 mol.) of 4-fluorobenzaldehyde, 21.0 g (0.35 mol.) of urea, 200 mg (2 mmol.) of copper(I) chloride, 2 mL of sulfuric acid, and 200 mL of methanol. The content of the flask was heated to 64-65° C. for 24 hours under reflux with stirring, to carry out the reaction. There was precipitated crystalline product. The crystalline product was collected on a filter paper and washed with methanol to obtain 49.7 g of 4-(4-fluorophenyl)-6-isopropyl-5-methoxycarbonyl-3,4-2(1H)-dihydropyrimidinone as a colorless crystalline product having the below-mentioned characteristics. The yield was 85% (based on the amount of methyl isobutyrylacetate).

m.p.: 223-225° C.

UV $\lambda_{max}$ ($CH_3CN$, m): 194.3, 278.6

IR (KBr, $cm^{-1}$): 3296, 3229, 3137, 2963, 1685, 1629, 1504, 1225, 1097.

$^1$H-NMR (DMSO-$d_6$, δ (ppm)): 1.14 (6H, dd, J=6.8, 6.9 Hz), 3.52 (3H, s), 4.0-4.2 (1H, m), 5.15 (1H, d, J=3.4 Hz), 7.1-7.2 (2H, m), 7.2-7.3 (2H, m), 7.76 (1H, d, J=3.2 Hz), 8.91 (1H, s).

HRMS: 292.1247 (theoretical value ($C_{15}H_{17}FN_2O_3$(M+)) 292.1223)

Example 2

Preparation of 4-(4-fluorophenyl)-6-isopropyl-5-methoxycarbonyl-3,4-2(1H)-dihydropyrimidinone The procedures of Example 1 were repeated except for replacing 200 mg (2 mmol.) of copper(I) chloride with 5.41 g (20 mmol.) of iron(III) chloride.hexahydrate. There was obtained 35.6 g of 4-(4-fluorophenyl)-6-isoproply-5-methoxycarbonyl-3,4-2(1H)-dihydropyrimidinone. The yield was 61% (based on the amount of methyl isobutyrylacetate).

Example 3

Preparation of 4-(4-fluorophenyl)-2-hydroxy-6-isopropyl-5-methoxycarbonylpyrimidine In a 50 mL-volume glass flask equipped with a stirrer and a thermometer was placed 11 mL (144 mmol.) of nitric acid (60-61%, sp.gr.: 1.38). To the nitric acid was slowly added at room temperature 4.00 g (13.7 mmol.) of 4-(4-fluorophenyl)-6-isopropyl-5-methoxycarbonyl-3,4-2(1H)-dihydropyrimidinone prepared in the same manner as in Example 1, and the mixture was subjected to reaction for 30 minutes at room temperature. After the reaction was complete, the reaction mixture was neutralized by placing the mixture in 140 mL of saturated aqueous sodium hydrogen carbonate solution. The reaction mixture was then extracted with ethyl acetate. The organic liquid portion was separated and concentrated under reduced pressure. The residue was crystallized from toluene. The crystalline product was collected on a filter and washed with toluene to obtain 3.64 g of 4-(4-fluorophenyl)-2-hydroxy-6-isopropyl-5-methoxycarbonylpyrimidine as a colorless crystalline product having the below-mentioned characteristics. The yield was 92% (based on the amount of 4-(4-fluorophenyl)-6-isopropyl-5-methoxycarbonyl-3,4-2(1H)-dihydropyrimidinone).

m.p.: 193° C. (decomposed)

UV $\lambda_{max}$ (CH$_3$CN, m): 196.6, 243.2, 317.9

IR (KBr, cm$^{-1}$): 2991, 2887, 1717, 1653, 1589, 1433, 1280, 1223.

$^1$H-NMR (DMSO-d$_6$, δ (ppm)): 1.23 (6H, d, J=6.8 Hz), 3.0-3.2 (1H, m), 3.56 (3H, s), 7.3-7.4 (2H, m), 7.5-7.6 (2H, m), 12.25 (1H, brs).

HRMS: 290.1054 (theoretical value (C$_{15}$H$_{15}$FN$_2$O$_3$(M+)) 290.1067)

Example 4

Preparation of 4-(4-fluorophenyl)-2-hydroxy-6-isopropyl-5-methoxycarbonylpyrimidine In a 50 mL-volume glass flask equipped with a stirrer and a thermometer were placed 2.92 g (10 mmol.) of 4-(4-fluorophenyl)-6-isopropyl-5-methoxycarbonyl-3,4-2(1H)-dihydropyrimidinone prepared in the same manner as in Example 1 and 5 mL of acetic acid. To the mixture was slowly added 3.74 mL (50 mmol.) of nitric acid (60-61%, sp.gr.: 1.38). To the mixture was further added 0.07 g (1 mmol.) of sodium nitrite, and the reaction was carried out for one hour at room temperature. After the reaction was complete, the reaction mixture was neutralized by placing the mixture in 50 mL of saturated aqueous sodium hydrogen carbonate solution. The reaction mixture was then extracted with ethyl acetate. The organic liquid portion was separated and concentrated under reduced pressure. The residue was crystallized from toluene. The crystalline product was collected on a filter and washed with toluene to obtain 2.61 g of 4-(4-fluorophenyl)-2-hydroxy-6-isopropyl-5-methoxycarbonyl-pyrimidine as a colorless crystalline product. The yield was 90% (based on the amount of 4-(4-fluorophenyl)-6-iso-propyl-5-methoxycarbonyl-3,4-2(1H)-dihydropyrimidinone).

Example 5

Preparation of 4-(4-fluorophenyl)-2-hydroxy-6-isopropyl-5-methoxycarbonylpyrimidine In a 200 mL-volume glass flask equipped with a stirrer and a thermometer was placed 54.0 g (735 mmol.) of nitric acid (60-61%, sp.gr.: 1.38). To the nitric acid was slowly added at room temperature 30.6 g (105 mmol.) of 4-(4-fluorophenyl)-6-isopropyl-5-methoxycarbonyl-3,4-2(1H)-dihydropyrimidinone prepared in the same manner as in Example 1, and the mixture was subjected to reaction for 30 minutes at room temperature. After the reaction was complete, the reaction mixture was poured into 162 mL of water. The aqueous mixture was neutralized by adding 61 g of aqueous sodium hydroxide solution (48 wt. %) to precipitate a crystalline product. The crystalline product was collected by filtration and dried to obtain 27.6 g of 4-(4-fluorophenyl)-2-hydroxy-6-isopropyl-5-methoxy-carbonylpyrimidine as a colorless crystalline product. The yield was 91% (based on the amount of 4-(4-fluorophenyl)-6-isopropyl-5-methoxycarbonyl-3,4-2 (1H)-dihydro-pyrimidinone).

Example 6

Preparation of 4-(4-fluorophenyl)-2-hydroxy-6-isopropyl-5-methoxycarbonylpyrimidine In a 2 L-volume glass flask equipped with a stirrer and a thermometer was placed 323.3 g (3.09 mol.) of nitric acid (60-61%, sp.gr.: 1.38). The concentrated nitric acid was then cooled to 10° C. To the nitric acid was added 2.36 g (34.2 mmol.) of sodium nitrite, and was further added slowly 100 g (342 mmol.) of 4-(4-fluorophenyl)-6-isopropyl-5-methoxycarbonyl-3,4-2(1H)-dihydropyrimidinone prepared in the same manner as in Example 1. The mixture was subjected to reaction for 2 hours at a temperature of 10-12° C. After the reaction was complete, 970 mL of water was poured into the reaction mixture. The aqueous mixture was then neutralized by adding 257 g of aqueous sodium hydroxide solution (48 wt. %) to precipitate a crystalline product. The crystalline product was collected by filtration and dried to obtain 93.3 g of 4-(4-fluorophenyl)-2-hydroxy-6-isopropyl-5-methoxycarbonylpyrimidine as a colorless crystalline product. The yield was 94% (based on the amount of 4-(4-fluorophenyl)-6-isopropyl-5-methoxycarbonyl-3,4-2(1H)-dihydropyrimidinone).

Example 7

Preparation of 4-(4-fluorophenyl)-6-isopropyl-5-methoxycarbonyl-2-(N-methyl-N-methanesulfonyl-amino)pyrimidine In a 200 mL-volume glass flask equipped with a stirrer, a thermometer and a reflux condenser were placed 5.81 g (20 mmol.) of 4-(4-fluorophenyl)-2-hydroxy-6-isopropyl-5-methoxycarbonylpyrimidine, 3.59 g (26 mmol.) of potassium carbonate (available from Asahi Glass Works, Co., Ltd., Lot No. 1111632, particle size distribution: 75-250 μm: 14%, 75 μm pass: 86%), and 40 mL of butyl acetate. To the mixture was slowly added 4.19 g (22 mmol.) of p-toluenesulfonyl chloride under stirring, and the reaction was carried out at 40° C. for 4 hours. Subsequently, the reaction mixture was cooled to room temperature. To the cooled reaction mixture were added 2.84 g (26 mmol.) of N-methylmethanesulfonamide and 4.15 g (30 mmol.) of potassium carbonate (same as above). The mixture was heated to 110-125° C. for 2 hours under refluxing to carry out a reaction. After the reaction was complete, the mixture was cooled to room temperature. To the cooled mixture were added 25 mL of water and 20 mL of acetone, and the organic liquid portion was separated. The organic liquid portion was washed with a saturated aqueous sodium chloride solution and dried over anhydrous magnesium sulfate. The dry organic liquid portion was filtered and concentrated under reduced pressure. The residue was crystallized from heptane, to obtain 6.58 g of 4-(4-fluorophenyl)-6-isopropyl-5-methoxycarbonyl-2-(N-methyl-N-methane-sulfonylamino)pyrimidine as a pale yellow crystalline product. The yield was 86% (based on the amount of 4-(4-fluorophenyl)-2-hydroxy-6-isopropyl-5-methoxycarbonylpyrimidine).

Example 8

Preparation of 4-(4-fluorophenyl)-6-isoproply-5-methoxycarbonyl-2-(N-methyl-N-methanesulfonyl-amino)pyrimidine In a 1000 mL-volume glass flask equipped with a stirrer, a thermometer and a reflux condenser were placed 50.0 g (172 mmol.) of 4-(4-fluorophenyl)-2-hydroxy-6-isopropyl-5-methoxycarbonylpyrimidine, 20.8 g (189 mmol.) of sodium t-pentoxide, and 344 mL of acetonitrile, and the resulting mixture was stirred at 0-10° C. for 30 minutes. To the mixture was slowly added 36.1 g (189 mmol.) of p-toluenesulfonyl chloride, and the reaction was carried out at for 5 hours at room temperature. Subsequently, the reaction mixture was cooled to a temperature of 0-10° C. To the cooled reaction mixture were added 28.2 g (258 mmol.) of N-methyl-methanesulfonamide and 26.5 g (241 mmol.) of sodium t-pentoxide. The mixture was kept at 0-10° C. for one hour and then heated to 75-82° C. for 2 hours under refluxing, to carry out a reaction. After the reaction was complete, the mixture was cooled to room temperature. To the cooled mixture was added 344 mL of water. The aqueous mixture was cooled to 0-10° C. and stirred for one hour, precipitating a crystalline product. The crystalline product was collected by filtration and dried, to obtain 45.3 g of 4-(4-fluorophenyl)-6-isopropyl-5-methoxycarbonyl-2-(N-methyl-N-methanesulfonylamino)pyrimidine as a pale yellow crystalline product. The yield was 68% (based on the amount of 4-(4-fluorophenyl)-2-hydroxy-6-isopropyl-5-methoxycarbonylpyrimidine).

Example 9

Preparation of 4-(4-fluorophenyl)-6-isopropyl-5-methoxycarbonyl-2-(N-methyl-N-methanesulfonylamino)pyrimidine from methyl isobutyrylacetate, 4-fluorobenzaldehyde and urea 1) In a 200 L-volume glass-lined reaction vessel equipped with a stirrer, a thermometer and a reflux condenser were placed 24.4 kg (169 mol.) of methyl isobutyrylacetate, 20.0 kg (161 mol.) of 4-fluorobenzaldehyde, 16.9 kg (282 mol.) of urea, 0.2 kg (2 mol.) of copper(I) chloride, 3.0 kg of sulfuric acid, and 80.4 kg of methanol. The mixture was heated to 64-66° C. for 20 hours under refluxing, to carry out reaction. After the reaction was complete, the reaction mixture was cooled to room temperature, to precipitate a crystalline product. The crystalline product was collected on a filter paper and washed with methanol to obtain 43.4 kg of 4-(4-fluorophenyl)-6-isopropyl-5-methoxycarbonyl-3,4-2(1H)-dihydropyrimidinone as a colorless crystalline product.

2) In a 200 L-volume glass-lined reaction vessel equipped with a stirrer and a thermometer were placed 62.5 kg (615.6 mol.) of diluted nitric acid and 0.5 kg (6.8 mol.) of sodium nitrite. To the mixture was slowly added under chilling 20.0 kg (68.4 mmol.) of the 4-(4-fluorophenyl)-6-isopropyl-5-methoxycarbonyl-3,4-2(1H)-dihydropyrimidinone prepared as above. The resulting mixture was subjected to reaction at a low temperature (10° C.). After the reaction was complete, the reaction mixture was neutralized by addition of an aqueous methanol solution of sodium hydroxide. Subsequently, an aqueous sodium hydroxide solution was added to the mixture. The resulting mixture was placed under reduced pressure to distill methanol off. To the residue were added 96.5 kg of acetone and 96.5 kg of water. The aqueous residue was then neutralized by addition of acetic acid to precipitate a crystalline product. The crystalline product was collected on a filter paper and washed with a acetone/water mixture, to give 17.9 kg of 4-(4-fluorophenyl)-2-hydroxy-6-isopropyl-5-methoxycarbonylpyrimidine.

3) In a 200 L-volume glass-lined reaction vessel equipped with a stirrer, a thermometer and a reflux condenser were placed 17.9 kg (62.0 mol.) of 4-(4-fluorophenyl)-2-hydroxy-6-isopropyl-5-methoxycarbonylpyrimidine prepared as above, 107.7 kg of butyl acetate, 11.1 kg (80.3 mol.) of potassium carbonate (available from Asahi Glass Works, Co., Ltd., Lot No. 1111632, particle size distribution: 75-250 μm: 14%, 75 μm pass: 86%), and 12.9 kg (67.7 mol.) of p-toluenesulfonyl chloride. The mixture was heated at 60° C. for 2 hours, to carry out reaction. Subsequently, the reaction mixture was cooled to room temperature. To the cooled mixture were added 8.8 kg (80.6 mol.) of N-methylmethanesulfonamide and 12.9 kg (93.3 mol.) of potassium carbonate, and the resulting mixture was heated at 122-125° C. for 3 hours, for carrying reaction. After the reaction was complete, the reaction mixture was cooled to room temperature. To the cooled mixture were added acetone and water, and the organic liquid portion was separated. The organic liquid portion was then washed successively with aqueous sodium hydroxide solution (3 wt. %) and a saturated aqueous sodium chloride solution. The washed organic liquid portion was concentrated under reduced pressure. Isopropyl alcohol and water were added to the residue, resulting in precipitation of a crystalline product. The crystalline product was filtered on a filter paper and washed with isopropyl alcohol. The washed crystalline product and 85.7 kg of acetone were placed in a 200 L-volume glass lined reaction vessel equipped with a stirrer, a thermometer and a reflux condenser. The mixture was stirred at 50-55° C., to dissolve the crystalline product in acetone. The insoluble was removed with a line filter. Subsequently, 58.3 kg of water was added to the solution, to precipitate a crystalline product. The crystalline product was collected on a filter paper and washed with an acetone/water mixture, to give 19.5 kg of 4-(4-fluorophenyl)-6-isopropyl-5-methoxycarbonyl-2-(N-methyl-N-methanesulfonylamino)pyrimidine.

Example 10

Preparation of 2-chloro-4-(4-fluorophenyl)-6-isopropyl-5-methoxycarbonylpyrimidine In a 25 mL-volume glass flask equipped with a stirrer, a thermometer and a reflux condenser were placed 1.00 g (3.43 mmol.) of 4-(4-fluorophenyl)-2-hydroxy-6-isopropyl-5-methoxycarbonylpyrimidine and 3.4 mL (3.7 mmol.) of phosphorus oxychloride. The mixture was heated to 100-106° C. for 1.5 hours under refluxing, to carry out reaction. After the reaction was complete, the reaction mixture was cooled to room temperature, and poured into an ice/water mixture. The resulting aqueous mixture was neutralized with a saturated aqueous sodium hydrogen carbonate solution. The neutralized aqueous mixture was extracted with ethyl acetate. The ethyl acetate portion was separated, washed with a saturated aqueous sodium chloride solution, and dried over anhydrous magnesium sulfate. The dried ethyl acetate portion was filtered and concentrated under reduced pressure, to obtain 1.03 g of 2-chloro-4-(4-fluorophenyl)-6-isopropyl-5-methoxycarbonylpyrimidine as a colorless crystalline product having the below-mentioned characteristics. The yield was 97%

(based on the amount of 4-(4-fluorophenyl)-2-hydroxy-6-isopropyl-5-methoxycarbonylpyrimidine).

m.p.: 99-101° C.

UV $\lambda_{max}$ (CH$_3$CN, m): 194.7, 276.5

IR (KBr, cm$^{-1}$): 2980, 1728, 1542, 1508, 1227, 1086.

$^1$H-NMR (DMSO-d$_6$, δ(ppm)): 1.33 (6H, d, J=6.8 Hz), 3.1-3.2 (1H, m), 3.76 (3H, s), 7.15 (2H, t, J=8.5 Hz), 7.6-7.7 (2H, m).

HRMS: 308.0695 (theoretical value (C$_{15}$H$_{14}$ClFN$_2$O$_2$ (M+)) 308.0728)

Example 11

Preparation of 2-chloro-4-(4-fluorophenyl)-6-isopropyl-5-methoxycarbonylpyrimidine In a 25 mL-volume glass flask equipped with a stirrer, a thermometer and a reflux condenser were placed 1.00 g (3.43 mmol.) of 4-(4-fluorophenyl)-2-hydroxy-6-isopropyl-5-methoxycarbonylpyrimidine, 0.5 mL (3.9 mmol.) of thionyl chloride, 3.44 mL of toluene, and 0.11 mL of N,N-dimethylformamide. The mixture was heated to 80° C. for 3 hours, to carry out reaction. After the reaction was complete, the reaction mixture was cooled to room temperature, and poured into an ice/water mixture. The resulting aqueous mixture was neutralized with a saturated aqueous sodium hydrogen carbonate solution. The neutralized aqueous mixture was extracted with ethyl acetate. The ethyl acetate portion was separated, washed with a saturated aqueous sodium chloride solution, and dried over anhydrous magnesium sulfate. The dried ethyl acetate portion was filtered and concentrated under reduced pressure, to obtain 0.80 g of 2-chloro-4-(4-fluorophenyl)-6-isopropyl-5-methoxycarbonylpyrimidine as a colorless crystalline product. The yield was 76% (based on the amount of 4-(4-fluorophenyl)-2-hydroxy-6-isopropyl-5-methoxycarbonylpyrimidine).

Example 12

Preparation of 4-(4-fluorophenyl)-6-isopropyl-5-methoxycarbonyl-2-(N-methyl-N-methanesulfonyl-amino)pyrimidine In a 25 mL-volume glass flask equipped with a stirrer, a thermometer and a reflux condenser were placed 546 mg (5 mmol.) of N-methylmethanesulfonamide, 551 mg (5 mmol.) of sodium t-pentoxide, 10 mL of acetonitrile, and 309 mg (1 mmol.) of 2-chloro-4-(4-fluorophenyl)-6-isopropyl-5-methoxycarbonylpyrimidine. The mixture was heated to 81-82° C. for 3 hours under refluxing, to carry out reaction. After the reaction was complete, the reaction mixture was cooled to room temperature. To the cooled mixture was added 10 mL of water, and the aqueous mixture was extracted with ethyl acetate. The ethyl acetate portion was separated, and dried over anhydrous magnesium sulfate. The dried ethyl acetate portion was filtered and concentrated under reduced pressure. The residue was purified by silica gel column chromatography (column: Wako Gel C-200, eluent: hexane/ethyl acetate (2:1, volume ratio)). There was obtained 339 mg of 4-(4-fluorophenyl)-6-isopropyl-5-methoxycarbonyl-2-(N-methyl-N-methanesul-fonylamino)pyrimidine. The yield was 89% (based on the amount of 2-chloro-4-(4-fluorophenyl)-6-isopropyl-5-methoxycarbonylpyrimidine).

Example 13

Preparation of 4-(4-fluorophenyl)-6-isopropyl-5-methoxycarbonyl-2-methanesulfonyloxypyrimidine In a 100 mL-volume glass flask were placed 10.0 g (34.4 mmol.) of 4-(4-fluorophenyl)-2-hydroxy-6-isopropyl-5-methoxycarbonylpyrimidine, 5.22 g (58.5 mmol.) of triethylamine, and 34 mL of acetonitrile. The mixture in the flask was chilled to 0-5° C. in an ice bath. To the chilled mixture was slowly added 5.12 g (44.7 mmol.) of methanesulfonyl chloride, and the resulting mixture was subjected to reaction at 20-25° C. for 2 hours. After the reaction was complete, to the reaction mixture was added 60 mL of water. The aqueous reaction mixture was extracted with toluene and the toluene portion was separated. The toluene portion was washed with a saturated aqueous sodium chloride solution and dried over anhydrous magnesium sulfate. The dried mixture was filtered and concentrated under reduced pressure. The residue was crystallized from methanol, to give 11.3 g of 4-(4-fluorophenyl)-6-isopropyl-5-methoxycarbonyl-2-methanesulfonyloxypyrimidine as a colorless crystalline product having the below-mentioned characteristics. The yield was 89% (based on the amount of 4-(4-fluorophenyl)-2-hydroxy-6-isopropyl-5-methoxycarbonylpyrimidine).

m.p.: 110-111° C.

UV $\lambda_{max}$ (CH$_3$CN, m): 193.7, 276.8

IR (KBr, cm$^{-1}$): 2980, 1724, 1562, 1391, 1250, 1175, 1079, 971.

$^1$H-NMR (CDCl$_3$, δ (ppm)): 1.33 (6H, d, J=6.6 Hz), 3.20 (1H, m), 3.60 (3H, s), 7.1-7.2 (2H, s), 7.6-7.8 (2H, m).

HRMS: 368.0842 (theoretical value (C$_{15}$H$_{17}$FN$_2$O$_5$S (M+)) 368.0892)

Example 14

Preparation of 4-(4-fluorophenyl)-6-isopropyl-5-methoxycarbonyl-2-(p-toluenesulfonyloxy)-pyrimidine In a 200 mL-volume glass flask were placed 27.6 g (95.1 mmol.) of 4-(4-fluorophenyl)-2-hydroxy-6-isopropyl-5-methoxycarbonylpyrimidine, 12.5 g (123 mmol.) of triethylamine, and 95 mL of acetonitrile. The mixture of the flask was chilled to 0-5° C. in an ice bath. To the chilled mixture was slowly added 20.0 g (105 mmol.) of p-toluenesulfonyl chloride, and the resulting mixture was subjected to reaction at 20-25° C. for one hour. After the reaction was complete, to the reaction mixture was added 95 mL of water. The aqueous reaction mixture was extracted with toluene and the toluene portion was separated. The toluene portion was washed with a saturated aqueous sodium chloride solution and dried over anhydrous magnesium sulfate. The dried mixture was filtered and concentrated under reduced pressure. The residue was crystallized from methanol, to give 35.9 g of 4-(4-fluorophenyl)-6-isopropyl-5-methoxycarbonyl-2-(p-toluenesulfonyloxy)-pyrimidine as a colorless crystalline product having the below-mentioned characteristics. The yield was 85% (based on the amount of 4-(4-fluorophenyl)-2-hydroxy-6-isopropyl-5-methoxycarbonylpyrimidine).

m.p.: 94-96° C.

UV $\lambda_{max}$ (CH.sub.3CN, m): 194.9, 275.2

IR (KBr, cm$^{-1}$): 2961, 1734, 1539, 1389, 1352, 1247, 1090, 980.

$^1$H-NMR (CDCl$_3$, δ (ppm)): 1.23 (6H, d, J=6.8 Hz), 2.45 (3H, s), 3.0-3.2 (1H, m), 3.74 J=8.5 Hz).

HRMS: 444.1155 (theoretical value ($C_{22}H_{21}FN_2O_5S$ (M+)) 444.1194)

Example 15

Preparation of 4-(4-fluorophenyl)-6-isopropyl-5-methoxycarbonyl-2-benzenesulfonyloxypyrimidine The procedures of Example 13 were repeated except for replacing p-toluenesulfonyl chloride with 18.5 g (105 mmol.) of benzenesulfonyl chloride.

There was obtained 39.3 g of 4-(4-fluorophenyl)-6-isopropyl-5-methoxycarbonyl-2-benzenesulfonyloxypyrimidine as a pale yellow crystalline product having the below-mentioned characteristics. The yield was 96% (based on the amount of 4-(4-fluorophenyl)-2-hydroxy-6-isopropyl-5-methoxycarbonylpyrimidine).

$^1$H-NMR (CDCl$_3$, δ (ppm)): 1.21 (6H, d, J=6.4 Hz), 3.0-3.1 (1H, m), 3.73 (3H, s), 7.1-7.2 (2H, m), 7.5-7.7 (5H, m), 8.1-8.2 (2H, m).

Example 16

Preparation of 4-(4-fluorophenyl)-6-isopropyl-5-methoxycarbonyl-2-(2,4,6-trimethylbenzenesulfonyloxy)pyrimidine The procedures of Example 13 were repeated except for replacing p-toluenesulfonyl chloride with 23.0 g (105 mmol.) of 2,4,6-trimethylbenzenesulfonyl chloride.

There was obtained 37.7 g of 4-(4-fluorophenyl)-6-isopropyl-5-methoxycarbonyl-2-(2,4,6-trimethylbenzen-esulfonyloxy)pyrimidine as a pale yellow crystalline product having the below-mentioned characteristics. The yield was 84% (based on the amount of 4-(4-fluorophenyl)-2-hydroxy-6-isopropyl-5-methoxycarbonylpyrimidine).

$^1$H-NMR (CDCl$_3$, δ (ppm)): 1.17 (6H, d, J=6.8 Hz), 2.34 (3H, s), 2.67 (6H, s), 3.0-3.1 (1H, m), 3.73 (3H, s), 7.00 (2H, s), 7.0-7.2 (2H, m), 7.4-7.5 (2H, m).

Example 17

Preparation of 4-(4-fluorophenyl)-6-isopropyl-5-methoxycarbonyl-2-(2,4,6-triisopropylbenzenesulfonyloxy)pyrimidine The procedures of Example 13 were repeated except for replacing p-toluenesulfonyl chloride with 31.8 g (105 mmol.) of 2,4,6-triisopropylbenzenesulfonyl chloride.

There was obtained 47.1 g of 4-(4-fluorophenyl)-6-isopropyl-5-methoxycarbonyl-2-(2,4,6-triisopropylben-zenesulfonyloxy)pyrimidine as a pale yellow crystalline product having the below-mentioned characteristics. The yield was 89% (based on the amount of 4-(4-fluorophenyl)-2-hydroxy-6-isopropyl-5-methoxycarbonylpyrimidine).

$^1$H-NMR (CDCl$_3$, δ (ppm)): 1.12 (6H, d, J=6.6 Hz), 1.19 (12H, d, J=6.8 Hz), 1.27 (6H, d, J=7.1 Hz), 2.8-2.95 (1H, m), 2.95-3.1 (1H, m), 3.73 (3H, s), 4.1-4.3 (2H, m), 7.0-7.1 (2H, m), 7.20 (2H, s), 7.4-7.5 (2H, m).

Example 18

Preparation of 4-(4-fluorophenyl)-6-isopropyl-5-methoxycarbonyl-2-(p-methoxybenzenesulfonyloxy)-pyrimidine The procedures of Example 13 were repeated except for replacing p-toluenesulfonyl chloride with 21.7 g (105 mmol.) of p-methoxybenzenesulfonyl chloride.

There was obtained 39.9 g of 4-(4-fluorophenyl)-6-isopropyl-5-methoxycarbonyl-2-(p-methoxybenzenesulfo-nyloxy)pyrimidine as a colorless crystalline product having the below-mentioned characteristics. The yield was 91% (based on the amount of 4-(4-fluorophenyl)-2-hydroxy-6-isopropyl-5-methoxycarbonylpyrimidine).

$^1$H-NMR (CDCl$_3$, δ (ppm)): 1.25 (6H, d, J=6.8 Hz), 3.0-3.2 (1H, m), 3.74 (3H, s), 3.88 (3H, s), 6.99 (2H, dd, J=2.0, 9.0 Hz), 7.0-7.2 (2H, m), 7.5-7.7 (2H, m), 8.07 (2H, dd, J=2.2, 9.0 Hz).

Example 19

Preparation of 4-(4-fluorophenyl)-6-isopropyl-5-methoxycarbonyl-2-(p-chlorobenzenesulfonyloxy)-pyrimidine The procedures of Example 13 were repeated except for replacing p-toluenesulfonyl chloride with 22.2 g (105 mmol.) of p-chlorobenzenesulfonyl chloride.

There was obtained 39.9 g of 4-(4-fluorophenyl)-6-isopropyl-5-methoxycarbonyl-2-(p-chlorobenzenesulfonyloxy)pyrimidine as a colorless crystalline product having the below-mentioned characteristics. The yield was 89% (based on the amount of 4-(4-fluorophenyl)-2-hydroxy-6-isopropyl-5-methoxycarbonylpyrimidine).

$^1$H-NMR (CDCl$_3$, δ (ppm)): 1.23 (6H, d, J=6.6 Hz), 3.0-3.2 (1H, m), 3.74 (3H, s), 7.1-7.2 (2H, m), 7.5-7.7 (4H, m), 8.0-8.1 (2H, m).

Example 20

Preparation of 4-(4-fluorophenyl)-6-isopropyl-5-methoxycarbonyl-2-(2-nitrobenzenesulfonyloxy)-pyrimidine The procedures of Example 13 were repeated except for replacing p-toluenesulfonyl chloride with 23.3 g (105 mmol.) of 2-nitrobenzenesulfonyl chloride.

There was obtained 28.0 g of 4-(4-fluorophenyl)-6-isopropyl-5-methoxycarbonyl-2-(2-nitrobenzenesulfony-loxy)pyrimidine as an opaque crystalline product having the below-mentioned characteristics. The yield was 62% (based on the amount of 4-(4-fluorophenyl)-2-hydroxy-6-isopropyl-5-methoxycarbonylpyrimidine).

$^1$H-NMR (CDCl$_3$, δ (ppm)): 1.17 (6H, d, J=6.8 Hz), 3.0-3.2 (1H, m), 3.75 (3H, s), 7.1-7.2 (2H, m), 7.5-7.6 (2H, m), 7.7-8.0 (3H, m), 8.33 (1H, dd, J=1.7, 8.1 Hz).

Example 21

Preparation of 4-(4-fluorophenyl)-6-isopropyl-5-methoxycarbonyl-2-(N-methyl-N-methanesulfonylamino)pyrimidine In a 25 mL-volume glass flask equipped with a stirrer, a thermometer and a reflux condenser were placed 196 mg (1.8 mmol.) of N-methylmethanesulfonamide, 198 mg (1.8 mmol.) of sodium t-pentoxide, 7.5 mL of acetonitrile, and 667 mg (1.5 mmol.) of 4-(4-fluorophenyl)-6-isopropyl-5-methoxycarbonyl-2-(p-toluenesulfonyloxy)pyrimidine. The mixture was heated to 81-82° C. for 1.5 hours under refluxing, to carry out reaction. After the reaction was complete, the reaction mixture was cooled to room temperature. To the cooled mixture was added 10 mL of water, and the aqueous mixture was extracted with ethyl acetate. The ethyl acetate portion was separated, and dried over anhydrous magnesium sulfate. The dried ethyl acetate portion was filtered and concentrated under reduced pressure. The residue was purified by silica gel column chromatography (column: Wako Gel C-200, eluent: hexane/ethyl acetate (2:1, volume ratio)). There was obtained 428 mg of 4-(4-fluorophenyl)-6-isopropyl-5-methoxycarbonyl-2-(N-methyl-N-methanesul-fonylamino)-pyrimidine. The yield was 75% (based on the amount of 4-(4-fluorophenyl)-6-isopropyl-5-methoxycarbonyl-2-(p-toluenesulfonyloxy)pyrimidine).

Example 22

Preparation of (2-amino-4-(4-fluorophenyl)-6-isopropyl-5-methoxycarbonylpyrimidine In a 25 mL-volume glass flask equipped with a stirrer, a thermometer and a gas inlet were placed under ice-chilling 1.00 g (2.71 mmol.) of 4-(4-fluorophenyl)-6-isopropyl-5-methoxycarbonyl-2-methanesulfonyloxypyrimidine and 8.1 mL of tetrahydrofuran. The mixture was stirred at room temperature for 12 hours under gaseous ammonia atmosphere, for carrying out reaction. After the reaction was complete, 10 mL of water was added to the reaction mixture. The aqueous mixture was then subjected to extraction with toluene. The toluene portion was separated, washed with a saturated aqueous sodium chloride solution, and dried over anhydrous magnesium sulfate. The dried toluene portion was filtered and concentrated under reduced pressure. The residue was purified by silica gel column chromatography (column: Wako Gel C-200, eluent: hexane/ethyl acetate (2:1, volume ratio)). There was obtained 0.63 g of 2-amino-4-(4-fluorophenyl)-6-isopropyl-5-methoxycarbonylpyrimidine. The yield was 80% (based on the amount of 4-(4-fluorophenyl)-6-isopropyl-5-methoxycarbonyl-2-methanesulfonyloxypyrimidine). 6-isopropyl-5-methoxycarbonylpyrimidine Example 23

Preparation of (4-(4-fluorophenyl)-6-isopropyl-5-methoxycarbonyl-2-N-methylaminopyrimidine In a 50 mL-volume glass flask equipped with a stirrer, a thermometer and a dropping funnel was placed 6.00 g (16.3 mmol.) of 4-(4-fluorophenyl)-6-isopropyl-5-methoxycarbonyl-2-methanesulfonyloxypyrimidine. Into the flask was slowly dropped under ice-chilling 5.06 g (65.2 mmol) of aqueous 40 wt. % methylamine solution. The resulting mixture was stirred for one hour at the same temperature for carrying out reaction. After the reaction was complete, 16 mL of water was added to the reaction mixture. The aqueous mixture was then subjected to extraction with toluene. The toluene portion was separated, washed with a saturated aqueous sodium chloride solution, and dried over anhydrous magnesium sulfate. The dried toluene portion was filtered and concentrated under reduced pressure to give 4.81 g of 4-(4-fluorophenyl)-6-isopropyl-5-methoxycarbonyl-2-N-methylaminopyrimidine. The yield was 97% (based on the amount of 4-(4-fluoro-phenyl)-6-isopropyl-5-methoxycarbonyl-2-methanesulfonyloxypyrimidine).

Example 24

Preparation of 4-(4-fluorophenyl)-6-isopropyl-5-methoxycarbonyl-2-trifluoromethanesulfonyloxy-pyrimidine In a 300 mL-volume glass flask equipped with a stirrer, a thermometer and a reflux condenser were placed 8.7 g (30.0 mmol.) of 4-(4-fluorophenyl)-2-hydroxy-6-isopropyl-5-methoxycarbonylpyrimidine, 3.0 g (30.0 mmol.) of triethylamine, and 150 mL of toluene. The mixture in the flask was chilled to 0° C. in an ice bath. To the chilled mixture was slowly added 8.46 g (30.0 mmol.) of trifluoromethanesulfonic anhydride, and the resulting mixture was subjected to reaction for 3 hours at the same temperature. After the reaction was complete, to the reaction mixture was added 90 mL of water. From the aqueous reaction mixture, an organic liquid portion was separated. The organic liquid portion was concentrated under reduced pressure. The residue was purified by silica gel column chromatography (column: Wako Gel C-200, eluent: hexane/ethyl acetate (8:2, volume ratio)). There was obtained 8.46 g of 4-(4-fluorophenyl)-6-isopropyl-5-methoxycarbonyl-2-trifluoromethanesulfonyloxy-pyrimidine having the below-mentioned characteristics as a colorless oil. The yield was 74% (based on the amount of 4-(4-fluorophenyl)-2-hydroxy-6-isopropyl-5-methoxycarbonylpyrimidine).

IR (KBr, cm$^{-1}$): 3421, 2978, 1737, 1570, 1429, 1222, 1136, 973, 851

$^1$H-NMR (CDCl$_3$, δ ppm)): 1.33 (6H, d, J=6.6 Hz), 3.1-3.2 (1H, m), 3.80 (3H, s), 7.1-7.2 (2H, m), 7.7-7.8 (2H, m)

HRMS: 422.0585 (theoretical value (C$_{16}$H$_{14}$F$_4$N$_2$O$_5$S (M+)) 422.0560)

Example 25

Preparation of 4-(4-fluorophenyl)-6-isopropyl-5-methoxycarbonyl-2-trifluoromethanesulfonyloxy-pyrimidine In a 300 mL-volume glass flask equipped with a stirrer, a thermometer and a reflux condenser were placed 2.9 g (10.0 mmol.) of 4-(4-fluorophenyl)-2-hydroxy-6-isopropyl-5-methoxycarbonylpyrimidine, 1.7 g (16.8 mmol.) of triethylamine, and 50 mL of toluene. The mixture in the flask was chilled to 0° C. in an ice bath. To the chilled mixture was slowly added 2.4 g (14.1 mmol.) of trifluoromethanesulfonyl chloride, and the resulting mixture was subjected to reaction for 3 hours at the same temperature. After the reaction was complete, to the reaction mixture was added 30 mL of water. From the aqueous reaction mixture, an organic liquid portion was separated. The organic liquid portion was concentrated under reduced pressure. The residue was purified by silica gel column chromatography (column: Wako Gel C-200, eluent: hexane/ethyl acetate (8:2, volume ratio)). There was obtained 2.8 g of 4-(4-fluorophenyl)-6-isopropyl-5-methoxycarbonyl-2-trifluoromethanesulfonyloxypyrimidine having the below-mentioned characteristics as a colorless oil. The yield was 66% (based on the amount of 4-(4-fluorophenyl)-2-hydroxy-6-isopropyl-5-methoxycarbonylpyrimidine).

Example 26

Preparation of 4-(4-fluorophenyl)-6-isopropyl-5-methoxycarbonyl-2-(N-methyl-N-methanesulfonylamino)pyrimidine In a 50 mL-volume glass flask equipped with a stirrer, a thermometer and a reflux condenser were placed 3.0 g (7 mmol.) of 4-(4-fluorophenyl)-6-isopropyl-5-methoxycarbonyl-2-trifluoromethanesulfonyloxypyrimidine, 1.13 g (10.5 mmol.) of N-methylmethanesulfonamide, 1.45 g (10.5 mmol.) of potassium carbonate (available from Wako Junyaku Co., Ltd., special grade), and 14 mL of butyl acetate. The mixture was heated to 122-125° C. for 3 hours under refluxing, to carry out reaction. After the reaction was complete, the reaction mixture was cooled to room temperature. To the reaction mixture were added 10 mL of water and 7 mL of acetone, and the organic liquid portion was separated. The organic liquid portion was washed with a saturated aqueous sodium chloride solution and concentrated under reduced pressure. The residue was purified by silica gel column chromatography (column: Wako Gel C-200, eluent: hexane/ethyl acetate (5:1, volume ratio)). There was obtained 2.1 g of 4-(4-fluorophenyl)-6-isopropyl-5-methoxycarbonyl-2-(N-methyl-N-methanesul-fonylamino)pyrimidine as a white crystalline product. The yield was 78% (based on the amount of 4-(4-fluorophenyl)-6-isopropyl-5-methoxycarbonyl-2-trifluoromethanesulfonyloxypyrimidine).

Example 27

Preparation of 4-(4-fluorophenyl)-6-isopropyl-5-methoxycarbonyl-2-(N-methyl-N-methanesulfonylamino)pyrimidine In a 50 mL-volume glass flask equipped with a stirrer, a thermometer and a reflux condenser were placed 1.1 g (2.5 mmol.) of 4-(4-fluorophenyl)-6-isopropyl-5-methoxycarbonyl-2-(p-toluenesulfonyloxy)-pyrimidine, 0.55 g (5.0 mmol.) of N-methylmethanesulfonamide, 0.69 g (5.0 mmol.) of potassium carbonate (available from Wako Junyaku Co., Ltd., special grade), 0.32 g (1.0 mmol.) of tetrabutylammonium bromide, 20 mL of toluene and 5 mL of water. The mixture was heated to 85° C. for 28 hours under refluxing, to carry out reaction. After the reaction was complete, the reaction mixture was cooled to room temperature. To the reaction mixture were added 10 mL of water and 7 mL of acetone, and the organic liquid portion was separated. The organic liquid portion was analyzed by high performance liquid chromatography. It was confirmed that 0.6 g of 4-(4-fluorophenyl)-6-isopropyl-5-methoxycarbonyl-2-(N-methyl-N-methanesulfonylamino)pyrimidine was produced. The yield was 63% (based on the amount of 4-(4-fluorophenyl)-6-isopropyl-5-methoxycarbonyl-2-(p-toluenesulfonyloxy)-pyrimidine).

INDUSTRIAL UTILITY

The pyrimidine compound, particularly, 2-(N-methyl-N-methanesulfonylamino)pyrimidine compound, prepared by the invention is of value as an intermediate compound for the production of a cholesterol reducing agent (HMG-CoA reductase agent). The compound of formula (3) can be converted to an HMG CoA reductase inhibitor by the processes disclosed in European Patent Application Publication No. 0521471, Bioorg. Med. Chem., 5, 437 (1997) and International Patent Application No. WO 00/49014. The disclosures of these references are incorporated herein by reference to demonstrate how a compound of formula (3) or formula (8) can be converted to an HMG CoA reductase inhibitor, in particular, rosuvastatin or a pharmaceutically acceptable salt thereof, such as rosuvastatin calcium.

The invention claimed is:

1. A process for preparing a 2-(N-methyl-N-methanesulfonylamino)pyrimidine compound having the formula (3):

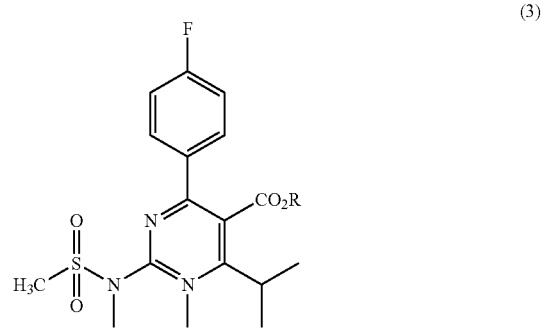

(3)

in which R is selected from the group consisting of an alkyl group having from 1 to 10 carbon atoms, a cycloalkyl group having 3 to 6 carbon atoms, an aryl-alkyl group having an alkyl moiety of from 1 to 3 carbon atoms, an aryl group and a methylphenyl group, which comprises the steps of:

(I) reacting an isobutyrylacetate ester of the following formula (5):

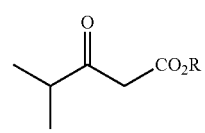

(5)

wherein R is the same as above, with 4-fluorobenzaldehyde and urea in the presence of a protonic compound selected from the group consisting of an inorganic acid or a salt thereof, an organic sulfonic acid, an organic carboxylic acid and an alcohol; and a metal salt selected from the group consisting of copper(I) chloride, copper(II) chloride, copper(II) acetate, iron(II) chloride, iron(III) chloride, aluminum chloride, nickel (II) bromide, tin(VI) chloride, titanium tetrachloride, and magnesium bromide;

(II) oxidizing the reaction product of the step (I);

(III) reacting the oxidation product of the step (II) with an organic sulfonyl halide having the formula (2):

R'SO₂X    (2)

in which R' is selected from the group consisting of an alkyl group having from 1 to 10 carbon atoms, a cycloalkyl group having 3 to 6 carbon atoms, an aryl-alkyl group having an alkyl moiety of from 1 to 3 carbon atoms, an aryl group and a methylphenyl group, and X is a halogen atom, or an organic sulfonic anhydride having the formula (2a):

(R'SO₂)₂O    (2a)

in which R' has the same meaning as above; and (IV) reacting the reaction product of the step (III) with N-methyl-N-methanesulfonamide.

2. A process for preparing a 2-(N-methyl-N-methanesulfonylamino)pyrimidine compound having the formula (3):

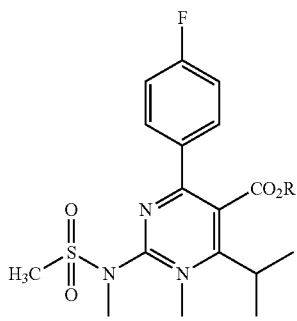
(3)

in which R is selected from the group consisting of an alkyl group having from 1 to 10 carbon atoms, a cycloalkyl group having 3 to 6 carbon atoms, an aryl-alkyl group having an alkyl moiety of from 1 to 3 carbon atoms, an aryl group and a methylphenyl group, which comprises the steps of:

reacting a hydroxypyrimidine compound having the formula (1):

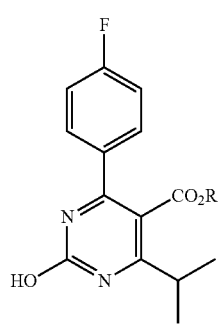
(1)

in which R is the same as above, with an organic sulfonyl halide having the formula (2):

R'SO$_2$X    (2)

in which R' is selected from the group consisting of an alkyl group having from 1 to 10 carbon atoms, a cycloalkyl group having 3 to 6 carbon atoms, an aryl-alkyl group having an alkyl moiety of from 1 to 3 carbon atoms, an aryl group and a methylphenyl group; and X is a halogen atom, or an organic sulfonic anhydride having the formula (2a):

(R'SO$_2$)$_2$O    (2a)

in which R' has the same meaning as above, and reacting the resulting reaction product with N-methyl-N-methanesulfonamide, wherein R' is a substituted or unsubstituted aryl group.

3. A process for preparing a 2-(N-methyl-N-methanesulfonylamino)pyrimidine compound having the formula (3):

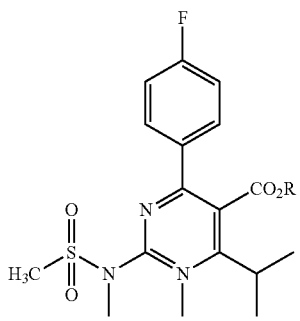
(3)

in which R is selected from the group consisting of an alkyl group having from 1 to 10 carbon atoms, a cycloalkyl group having 3 to 6 carbon atoms, an aryl-alkyl group having an alkyl moiety of from 1 to 3 carbon atoms, an aryl group and a methylphenyl group, which comprises the steps of:

reacting a hydroxypyrimidine compound having the formula (1):

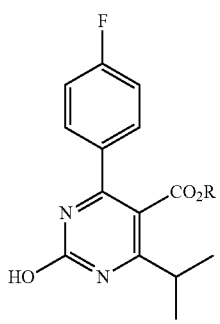
(1)

in which R is the same as above, with an organic sulfonyl halide having the formula (2):

R'SO$_2$X    (2)

in which R' is selected from the group consisting of an alkyl group having from 1 to 10 carbon atoms, a cycloalkyl group having 3 to 6 carbon atoms, an aryl-alkyl group having an alkyl moiety of from 1 to 3 carbon atoms, an aryl group and a methylphenyl group and X is a halogen atom, or an organic sulfonic anhydride having the formula (2a):

(R'SO$_2$)$_2$O    (2a)

in which R' has the same meaning as above, and reacting the resulting reaction product with N-methyl-N-methanesulfonamide, followed by conversion of the compound of formula (3) to rosuvastatin or a pharmaceutically acceptable salt thereof.

4. The process for preparing a 2-(N-methyl-N-methanesulfonylamino)pyrimidine compound having the formula (3):

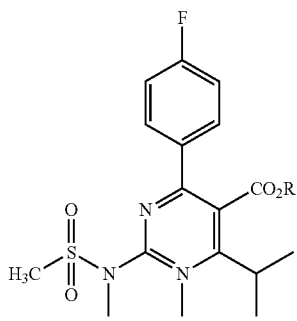

(3)

in which R is selected from the group consisting of an alkyl group having from 1 to 10 carbon atoms, a cycloalkyl group having 3 to 6 carbon atoms, an aryl-alkyl group having an alkyl moiety of from 1 to 3 carbon atoms, an aryl group and a methylphenyl group, which comprises the steps of:
(I) reacting an isobutyrylacetate ester of the following formula (5):

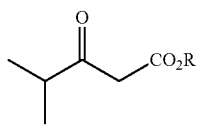

(5)

wherein R is the same as above, with 4-fluorobenzaldehyde and urea in the presence of a protonic compound selected from the group consisting of an inorganic acid or a salt thereof, an organic sulfonic acid, an organic carboxylic acid and an alcohol; and
a metal salt selected from the group consisting of copper(I) chloride, copper(II) chloride, copper(II)acetate, iron(II) chloride, iron(III) chloride, aluminum chloride, nickel (II) bromide, tin(VI) chloride, titanium tetrachloride, and magnesium bromide;
(II) oxidizing the reaction product of the step (I);
(III) reacting the oxidation product of the step (II) with an organic sulfonyl halide having the formula (2):

$$R'SO_2X \qquad (2)$$

in which R' is selected from the group consisting of an alkyl group having from 1 to 10 carbon atoms, a cycloalkyl group having 3 to 6 carbon atoms, an aryl-alkyl group having an alkyl moiety of from 1 to 3 carbon atoms, an aryl group and a methylphenyl group, and X is a halogen atom, or an organic sulfonic anhydride having the formula (2a):

$$(R'SO_2)_2O \qquad (2a)$$

in which R' has the same meaning as above; and
(IV) reacting the reaction product of the step (III) with N-methyl-N-methanesulfonamide to provide the compound having the formula (3),
followed by converting the compound having the formula (3) to rosuvastatin or a pharmaceutically acceptable salt thereof.

* * * * *